United States Patent
Kaihatsu et al.

(10) Patent No.: US 10,577,396 B2
(45) Date of Patent: Mar. 3, 2020

(54) TOLAN COMPOUND

(71) Applicant: OSAKA UNIVERSITY, Osaka (JP)

(72) Inventors: Kunihiro Kaihatsu, Osaka (JP); Nobuo Kato, Osaka (JP); Kenji Takagi, Osaka (JP)

(73) Assignee: Osaka University, Osaka (JP)

( * ) Notice: Subject to any disclaimer, the term of this patent is extended or adjusted under 35 U.S.C. 154(b) by 24 days.

(21) Appl. No.: 15/760,628

(22) PCT Filed: Sep. 16, 2016

(86) PCT No.: PCT/JP2016/077597
§ 371 (c)(1),
(2) Date: Mar. 15, 2018

(87) PCT Pub. No.: WO2017/047807
PCT Pub. Date: Mar. 23, 2017

(65) Prior Publication Data
US 2018/0258141 A1 Sep. 13, 2018

(30) Foreign Application Priority Data
Sep. 17, 2015 (JP) ................. 2015-184545

(51) Int. Cl.
| C07K 14/00 | (2006.01) |
| C07C 255/54 | (2006.01) |
| C12N 15/09 | (2006.01) |
| C07C 59/66 | (2006.01) |
| C07C 59/125 | (2006.01) |
| C12Q 1/6827 | (2018.01) |

(52) U.S. Cl.
CPC .......... C07K 14/003 (2013.01); C07C 59/125 (2013.01); C07C 59/66 (2013.01); C07C 255/54 (2013.01); C12N 15/09 (2013.01); C12Q 1/6827 (2013.01)

(58) Field of Classification Search
CPC .................................................. C07K 14/003
USPC ....................................................... 536/23.1
See application file for complete search history.

(56) References Cited

FOREIGN PATENT DOCUMENTS

| JP | 2010-143864 | 7/2010 |
| JP | 2012-75376 | 4/2012 |

OTHER PUBLICATIONS

Okazaki et al., "Sequence-specific detection of a single base pair mismatches by tolane-modified peptide nucleic acid," Program and Abstracts of the 40th International Symposium on Nucleic Acids Chemistry 2013, pp. 348-349.
Okazaki et al., "Intercalator Shushoku Peptide Kakusan ni yoru DNA Ichienki Shikibetsu," The 94th Annual Meeting of the Chemical Society of Japan in Spring Koen Yokoshu, 2014, p. 968, 1 PB-072.
Eryazici et al., "Enhancing the Melting Properties of Small Molecule-DNA Hybrids through Designed Hydrophobic Interactions: An Experimental-Computational Study," Journal of the American Chemical Society, 2012,vol. 134, pp. 7450-7458.
"Kagaku Shushoku Peptide Kakusan ni yoru Virus Genom 1-enki Heni no Kokando Shindanho no Kaihatsu", [online], Jun. 1, 2016, [retrieval date Oct. 12, 2016], Internet:<URL http://kaken.nii.ac.jp/ja/grant/KAKENHI-PROJECT-25290073/>.
Kam et al., "Detection of Endogenous K-ras mRNA in Living Cells at a Single Base Resolution by a PNA Molecular Beacon," Molecular Pharmaceutics, 2012, 9, pp. 685-693.
Igloi, "Variability in the stability of DNA-peptide nucleic acid (PNA) single-base mismatched duplexes: Real-time hybridization during affinity electrophoresis in PNA-containing gels," Proceedings of National Academy of Sciences USA, 1998, 95, pp. 8562-8567.
Kaihatsu et al., "Sequence-Specific and Visual Identification of the Influenza Virus NS Gene by Azobenzene-Tethered Bis-Peptide Nucleic Acid," PLOS ONE, May 2013, vol. 8, Issue 5, e64017 (5 pages).
Dogan et al., "5'-Tethered Stilbene Derivatives as Fidelity- and Affinity-Enhancing Modulators of DNA Duplex Stability," Journal of the American Chemical Society, 2004, vol. 126, pp. 4762-4763.
English Abstract for JP 2010-143864A, Jul. 1, 2010, 1 page.
English machine translation for JP 2012-075376A, Apr. 19, 2012, 27 pages.
International Search Report issued in corresponding Application No. PCT/JP2016/077597, dated Oct. 17, 2016, 4 pages.

*Primary Examiner* — Jezia Riley
(74) *Attorney, Agent, or Firm* — McNeill Baur PLLC

(57) ABSTRACT

An object of the present invention is to conduct a search for a compound to be arranged at a terminal of a peptide nucleic acid effective in detecting a single nucleotide polymorphism. Provided is a tolan compound represented by the following formula (1):

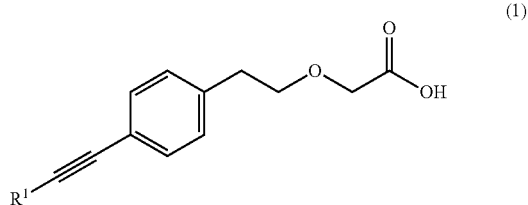

(1)

wherein $R^1$ represents a phenyl group or a naphthyl group, the phenyl group may have 1 to 5 substituents that are identical to or different from each other, and the naphthyl group may have 1 to 7 substituents that are identical to or different from each other.

15 Claims, 3 Drawing Sheets
Specification includes a Sequence Listing.

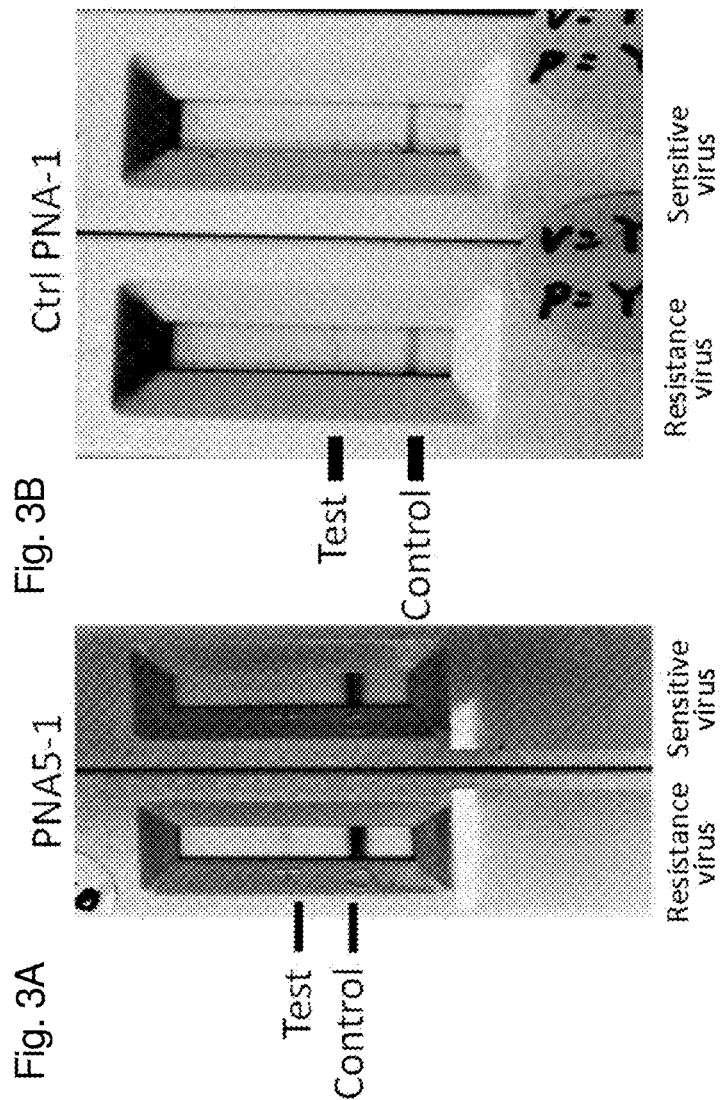

SEQUENCE LISTING

```
<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: PNA oligmer (control)

<400> SEQUENCE: 1
atctcctccc tt                                                         12

<210> SEQ ID NO 2
<211> LENGTH: 21
<212> TYPE: DNA
<213> ORGANISM: Artificial Sequence
```

```
<220> FEATURE:
<223> OTHER INFORMATION: complementary DNA

<400> SEQUENCE: 2
atgtcctaga ggagggaata a                                              21

<210> SEQ ID NO 3
<211> LENGTH: 21
<212> TYPE: DNA
<213> ORGANISM: Artificial Sequence
<220> FEATURE:
<223> OTHER INFORMATION: uncomplementary DNA

<400> SEQUENCE: 3
atgtcctaga ggagggcata a                                              21

<210> SEQ ID NO 4
<211> LENGTH: 21
<212> TYPE: DNA
<213> ORGANISM: Artificial Sequence
<220> FEATURE:
<223> OTHER INFORMATION: uncomplementary DNA

<400> SEQUENCE: 4
atgtcctaga ggagggabta a                                              21

<210> SEQ ID NO 5
<211> LENGTH: 21
<212> TYPE: DNA
<213> ORGANISM: Artificial Sequence
<220> FEATURE:
<223> OTHER INFORMATION: uncomplementary DNA

<400> SEQUENCE: 5
atgtcctaga ggagggbata a                                              21

<210> SEQ ID NO 6
<211> LENGTH: 21
<212> TYPE: DNA
<213> ORGANISM: Artificial Sequence
<220> FEATURE:
<223> OTHER INFORMATION: uncomplementary DNA

<400> SEQUENCE: 6
atgtcctaga ggagghaata a                                              21

<210> SEQ ID NO 7
<211> LENGTH: 12
<212> TYPE: DNA
<213> ORGANISM: Artificial Sequence
<220> FEATURE:
<223> OTHER INFORMATION: Partial sequence of Oseltamivir resistance
      influenza virus

<400> SEQUENCE: 7
ctcataataa aa                                                        12

<210> SEQ ID NO 8
<211> LENGTH: 12
<212> TYPE: DNA
<213> ORGANISM: Artificial Sequence
<220> FEATURE:
<223> OTHER INFORMATION: PNA for detection of Oseltamivir resistance
      influenza virus

<400> SEQUENCE: 8
```

```
gagtattatt tt                                                            12

<210> SEQ ID NO 9
<211> LENGTH: 12
<212> TYPE: DNA
<213> ORGANISM: Artificial Sequence
<220> FEATURE:
<223> OTHER INFORMATION: Partial sequence of Oseltamivir sensitive
      influenza virus

<400> SEQUENCE: 9
ctcataatca aa                                                            12

<210> SEQ ID NO 10
<211> LENGTH: 12
<212> TYPE: RNA
<213> ORGANISM: Artificial Sequence
<220> FEATURE:
<223> OTHER INFORMATION: Partial sequence of Oseltamivir resistance
      influenza virus

<400> SEQUENCE: 10
cucauaauaa aa                                                            12

<210> SEQ ID NO 11
<211> LENGTH: 12
<212> TYPE: DNA
<213> ORGANISM: Artificial Sequence
<220> FEATURE:
<223> OTHER INFORMATION: Partial sequence of Oseltamivir sensitive
      influenza virus

<400> SEQUENCE: 11
cucauaauca aa                                                            12

<210> SEQ ID NO 12
<211> LENGTH: 14
<212> TYPE: DNA
<213> ORGANISM: Artificial Sequence
<220> FEATURE:
<223> OTHER INFORMATION: Flu Resistance RNA Sequence

<400> SEQUENCE: 12
tcctcataat aaaa                                                          14

<210> SEQ ID NO 13
<211> LENGTH: 14
<212> TYPE: DNA
<213> ORGANISM: Artificial Sequence
<220> FEATURE:
<223> OTHER INFORMATION: Match PNA Sequence

<400> SEQUENCE: 13
ttttattatg agga                                                          14

<210> SEQ ID NO 14
<211> LENGTH: 14
<212> TYPE: DNA
<213> ORGANISM: Artificial Sequence
<220> FEATURE:
<223> OTHER INFORMATION: Mismatch PNA Sequence

<400> SEQUENCE: 14
tttcattatg agga                                                          14
```

TOLAN COMPOUND

This application is the national phase entry pursuant to 35 U.S.C. § 371 of International Application No. PCT/JP2016/077597, filed Sep. 16, 2016, which claims the benefit of priority to Japanese Patent Application No. 2015-184545, filed Sep. 17, 2015, both of which are incorporated herein by reference in their entirety.

TECHNICAL FIELD

The present invention relates to a tolan compound. The present invention also relates to a peptide nucleic acid modified with the tolan compound. The present invention also relates to a kit including the peptide nucleic acid.

BACKGROUND ART

In order to detect single nucleotide polymorphisms (SNPs) considered to provide information useful in a genetic diagnosis, a made-to-order therapy, a tailor-made therapy, or the like, a difference between a Tm value obtained at the time of the matching of a base pair (at the time of the formation of a perfect complementary strand) and a Tm value obtained at the time of the mismatching of the base pair (at the time of the formation of an imperfect complementary strand) (hereinafter referred to as "ΔTm value") is considered to be preferably as large as possible. In particular, when the ΔTm value is 10° C. or more, it has been known that an excellent diagnostic method in which a misdiagnosis rate at the time of a genetic diagnosis based on a single nucleotide polymorphism is less than 1% can be provided.

In recent years, a peptide nucleic acid known as one kind of nucleic acid analogs has been attracting attention from the viewpoint of its high stability. The development of a technology involving detecting a single nucleotide polymorphism with such peptide nucleic acid has been advanced (Non Patent Literatures 1 and 2).

With regard to the technology involving detecting a single nucleotide polymorphism with a peptide nucleic acid, such peptide nucleic acid as described in Non Patent Literature 2 does not show a ΔTm value enough to detect a single nucleotide polymorphism. Specifically, its ΔTm value when a mismatch is present in the base of a target DNA strand positioned second from an N-terminal is about 6.4° C. or less.

CITATION LIST

Non-Patent Literature

NPL 1: Molecular Pharmaceutics (2012) 9, 685-693
NPL 2: G. L. Igloi, Proc. Natl. Acad. Sci. USA (1998), 95, 8562-8567

SUMMARY OF INVENTION

Technical Problem

An object of the present invention is to provide a peptide nucleic acid effective in detecting a single nucleotide polymorphism, in particular, a peptide nucleic acid that can increase a Tm value obtained at the time of the matching of a base pair. Another object of the present invention is to provide an intermediate (production raw material) useful in producing the peptide nucleic acid.

Solution to Problem

The inventors of the present invention have made extensive investigations for achieving the objects, and as a result, have found that a peptide nucleic acid produced by bonding a specific tolan compound to an N-terminal is useful in detecting a single nucleotide polymorphism. The present invention has been completed on the basis of such finding, and includes the inventions of the following aspects.

I. Tolan Compound (I-1) A tolan compound, which is represented by the following formula (1):

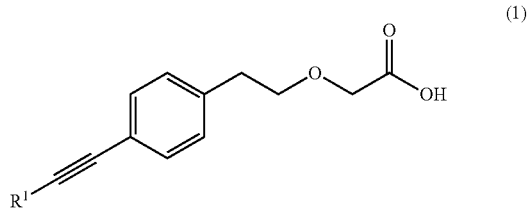

(1)

where:
R$^1$ represents a phenyl group or a naphthyl group;
the phenyl group may have 1 to 5 substituents that are identical to or different from each other; and
the naphthyl group may have 1 to 7 substituents that are identical to or different from each other.

(I-2) The tolan compound according to Item (I-1), in which the substituents are each an electron-withdrawing group.

(I-3) The tolan compound according to Item (I-2), in which the electron-withdrawing group is at least one member selected from the group consisting of a cyano group, a nitro group, an acyl group, a halogen group, a tosyl group, a mesyl group, and a phenyl group.

II. Method of Producing Tolan Compound (I)

(II-1) A method of producing the tolan compound (I) described in Item (I-1), the method including the step of causing a compound (2) represented by the following formula (2) and a deprotecting agent to react with each other:

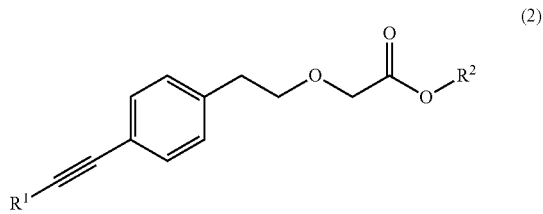

(2)

where R$^1$ has the same meaning as that described in Item (I-1) and R$^2$ represents a protective group for a carboxyl group.

(II-2) The production method according to Item (II-1), in which the substituents of R$^1$ in the formula (1) described in Item (I-1) are each an electron-withdrawing group.

(II-3) The production method according to Item (II-2), in which the electron-withdrawing group is at least one member selected from the group consisting of a cyano group, a nitro group, an acyl group, a halogen group, a tosyl group, a mesyl group, and a phenyl group.

III. Peptide Nucleic Acid (III-1) A tolan-modified peptide nucleic acid, which is represented by the following formula (3):

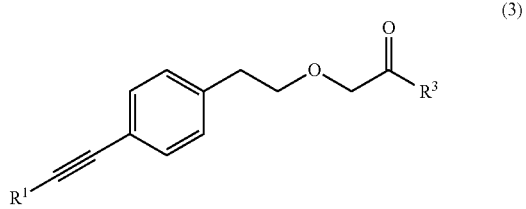

(3)

where $R^1$ is as described in Item (I-1) and $R^3$ represents a peptide nucleic acid residue.

(III-2) The peptide nucleic acid according to Item (III-1), in which the peptide nucleic acid residue is a residue represented by the following formula (4):

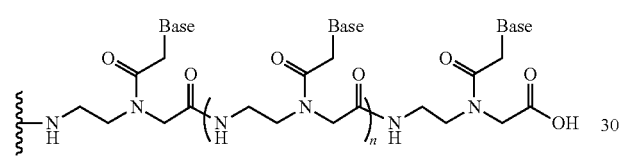

(4)

where:
Bases are identical to or different from each other, and each represent adenine, thymine, guanine, cytosine, or uracil; and n means an integer of from 6 to 25.

(III-3) The peptide nucleic acid according to Item (III-1) or (III-2), in which the substituents of $R^1$ in the formula (1) described in Item (I-1) are each an electron-withdrawing group.

(III-4) The peptide nucleic acid according to Item (III-3), in which the electron-withdrawing group is at least one member selected from the group consisting of a cyano group, a nitro group, an acyl group, a halogen group, a tosyl group, a mesyl group, and a phenyl group.

(III-5) The peptide nucleic acid according to any one of Items (III-1) to (III-4), in which the peptide nucleic acid residue contains an amino acid residue and/or a spacer.

(III-6) The peptide nucleic acid according to any one of Items (III-1) to (III-5), in which the peptide nucleic acid is subjected to a chemical modification.

(III-7) The peptide nucleic acid according to Item (III-6), in which the chemical modification is at least one member selected from the group consisting of acetylation, formylation, myristoylation, pyroglutamation, alkylation, glycosylation, amidation, acylation, hydroxylation, deamination, prenylation, palmitoylation, phosphorylation, biotinylation, and succinimidylation.

IV. Kit (IV-1) A kit, including at least one peptide nucleic acid (3) described in any one of Items (III-1) to (III-7).

(IV-2) The kit according to Item (IV-1), in which the kit is used for detecting at least one member selected from the group consisting of a drug-resistant bacterium, a drug-resistant virus, and a drug-resistant mycoplasma.

(IV-3) The kit according to Item (IV-2), in which the drug-resistant virus is an influenza virus.

(IV-4) The kit according to Item (IV-3), in which the influenza virus is oseltamivir-resistant.

Advantageous Effects of Invention

The peptide nucleic acid (3) is useful in detecting the mismatch of a single nucleotide polymorphism.

The kit including the peptide nucleic acid (3) is useful in, for example, a genetic diagnosis or a made-to-order therapy (tailor-made therapy) based on the detection of the mismatch of a single nucleotide polymorphism.

The tolan compound (1) is useful as a raw material (intermediate) for producing the peptide nucleic acid (3).

BRIEF DESCRIPTION OF DRAWINGS

FIGS. 3A and 3B are photographic images for showing the results of the experiment for detecting the oseltamivir-resistant influenza virus according to the immunochromatography method described in Experiment Example 3.

DESCRIPTION OF EMBODIMENTS

I. Tolan Compound

Figure 1:
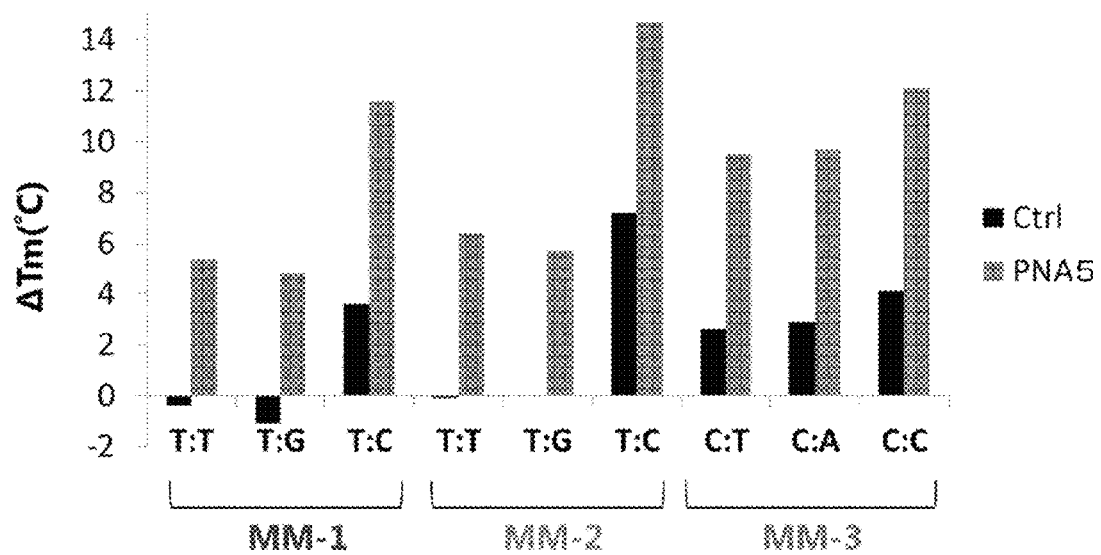
FIG. 1 is a graph of direct comparison between the sequence selectivities ($\Delta Tm$ values) of a peptide nucleic acid (control; ctrl) and a peptide nucleic acid 5 (PNA5) (Experiment Example 2).

A tolan compound (I) is a compound represented by the following formula (1).

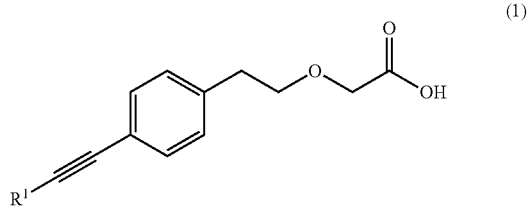

(1)

$R^1$ in the formula (1) represents a phenyl group or a naphthyl group.

The phenyl group may have 1, 2, 3, 4, or 5 substituents that are identical to or different from each other.

The naphthyl group may have 1, 2, 3, 4, 5, 6, or 7 substituents that are identical to or different from each other.

The positions at which the substituents are arranged are not particularly limited. For example, when the $R^1$ represents a phenyl group, a substituent may be arranged at an ortho position, a meta position, and/or a para position with respect to the phenyl group bonded to a tolan structure. In addition, when the $R^1$ represents a naphthyl group, a substituent may be arranged at a 1-position, a 2-position, a 3-position, a 4-position, a 5-position, a 6-position, and/or a 7-position with respect to the naphthyl group bonded to the tolan structure.

From the viewpoint of the usefulness of a tolan-modified peptide nucleic acid of the present invention in Examples to be described later, when the $R^1$ represents a phenyl group, a substituent is preferably arranged at the para position out of the positions at which the substituents are arranged, and when the $R^1$ represents a naphthyl group, a substituent is preferably arranged at the 4-position out of the positions.

The substituents are not particularly limited. An example thereof may be an electron-withdrawing group. At least one member selected from the group consisting of a cyano group, a nitro group, an acyl group, a halogen group, a tosyl group, a mesyl group, and a phenyl group may be given as a specific example of the electron-withdrawing group.

When the $R^1$ represents a phenyl group, a cyano group or a linear alkynyl group is preferably used as a substituent, and a cyano group is more preferably used from the viewpoint that steric hindrance with an adjacent base is avoided and hence a stacking effect is improved. When the $R^1$ represents a naphthyl group, a cyano group or a linear alkynyl group is preferably used as a substituent, and a cyano group is more preferably used from the viewpoint that the steric hindrance with the adjacent base is avoided and hence the stacking effect is improved.

II. Method of Producing Tolan Compound (1)

A method of producing the tolan compound (1) is as follows: the tolan compound (1) may be produced by causing a compound (2) represented by the following formula (2) and a deprotecting agent to react with each other.

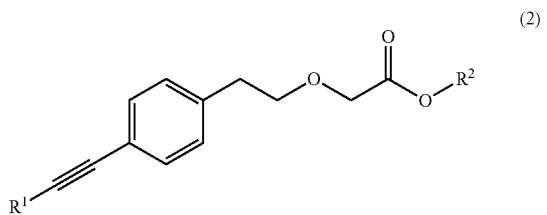

(2)

As described above, $R^1$ in the formula (2) represents a phenyl group that may have 1 to 5 substituents, or a naphthyl group that may have 1 to 7 substituents.

$R^2$ in the formula (2) represents a protective group for a carboxyl group.

The protective group for a carboxyl group is not particularly limited. Examples of such group may include an alkyl group, a benzyl group, an allyl group, and a silyl group. Of those protective groups, an alkyl group or an allyl group is preferred, and an alkyl group is more preferred from the viewpoint of the stability of an ester. Of the alkyl groups, a methyl group is most preferred.

The deprotecting agent is not particularly limited. A known deprotecting agent used for removing the protective group for a carboxyl group may be typically adopted. Specific examples of the deprotecting agent may include lithium hydroxide (LiOH), trifluoroacetic acid, palladium ($H_2$/Pd—C), tetrakis(triphenylphosphine)palladium, and acetic acid.

Of such deprotecting agents, lithium hydroxide, potassium hydroxide, or sodium hydroxide is preferred, and lithium hydroxide is more preferred.

The usage amount of the deprotecting agent is not particularly limited. The usage amount may be, for example, typically from about 1 molar equivalent to about 5 molar equivalents, preferably from about 1.5 molar equivalents to about 4 molar equivalents, more preferably from about 2 molar equivalents to about 3 molar equivalents with respect to the usage amount (1 mol) of the compound (2).

Conditions for the deprotection reaction are not particularly limited. For example, conditions used for removing the protective group for a carboxyl group may be appropriately adopted. Such conditions may be typically, for example, the following conditions: the compound (2) and the deprotecting agent are appropriately cooled or warmed to from about 0° C. to about 40° C. in a solvent, such as THF.

In order to obtain a target product compound with high purity, a commonly used isolating step and/or a commonly used purifying step may be adopted after the completion of the reaction while the steps are appropriately combined. Examples of such isolating or purifying step may include chromatography, recrystallization, extraction, and distillation.

The compound (2) is a compound easily produced from a known compound in conformity with a known method. For example, the compound (2) may be produced from a compound represented by the following formula (5) serving as a starting raw material by adopting a cross-coupling reaction called the Sonogashira coupling reaction out of known cross-coupling reactions while appropriately modifying the reaction.

More specifically, for example, the following method may be given: the compound (2) is produced by a method involving causing the compound (5) represented by the following formula (5),

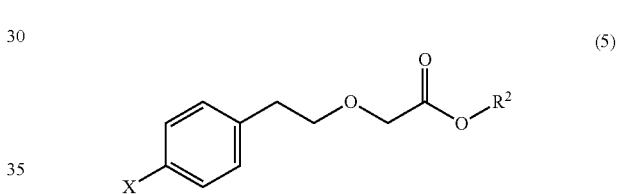

(5)

and a compound (6) represented by the following formula (6) or a compound (7) represented by the following formula (7) to react with each other in the presence of a palladium catalyst, a copper(I) compound, and a base.

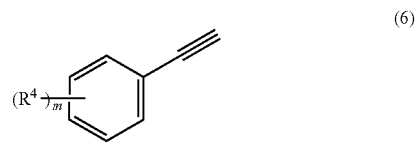

(6)

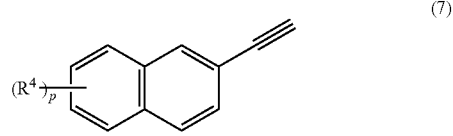

(7)

X in the formula (5) represents a halogen atom.

The halogen atom represented by the X is not particularly limited. The atom may be, for example, a chlorine atom, a bromine atom, a fluorine atom, or an iodine atom. As described above, $R^2$ in the formula (5) represents a protective group for a carboxyl group.

$R_4$'s in each of the formula (6) and the formula (7) are identical to or different from each other, and each represent a substituent. Such substituent is not particularly limited. An example thereof may be an electron-withdrawing group. At least one member selected from the group consisting of a trifluoro group, a cyano group, a nitro group, an acyl group, a halogen group, a tosyl group, a mesyl group, and a phenyl group may be given as a specific example of the electron-withdrawing group.

An electron-withdrawing group in the formula (6) is preferably a cyano group, a halogen group, or a trifluoro group, more preferably a cyano group from the viewpoint that steric hindrance with an adjacent base pair is avoided. An electron-withdrawing group in the formula (7) is preferably a cyano group, a halogen group, or a trifluoro group, more preferably a cyano group from the viewpoint that the steric hindrance with the adjacent base pair is avoided.

The number (m) of the substituents in the formula (6) may be set to 1, 2, 3, 4, or 5. In addition, the position at which any such substituent is arranged may be set to an ortho position, a meta position, and/or a para position with respect to a phenyl group bonded to a tolan structure.

The number (p) of the substituents in the formula (7) may be set to 1, 2, 3, 4, 5, 6, or 7. In addition, the position at which any such substituent is arranged may be set to a 1-position, a 2-position, a 3-position, a 4-position, a 5-position, a 6-position, and/or a 7-position with respect to a naphthyl group bonded to the tolan structure.

With regard to the positions at which the substituents are arranged, as described above, in the case of the formula (6), a substituent is preferably arranged at the para position, and in the case of the formula (7), a substituent is preferably arranged at the 4-position.

The palladium catalyst is not particularly limited. Examples thereof may include sodium tetrachloropalladate (II), tetrakis(triphenylphosphine)palladium(0), bistriphenylphosphinepalladium(II) chloride, and palladium(II) acetate. Of those palladium catalysts, sodium tetrachloropalladate (II) or tetrakis(triphenylphosphine)palladium(0) is preferred, and sodium tetrachloropalladate(II) is more preferred from the viewpoint of reactivity.

The usage amount of the palladium catalyst is not particularly limited. The usage amount may be, for example, typically from about 0.001 molar equivalent to about 0.5 molar equivalent, preferably from about 0.005 molar equivalent to about 0.05 molar equivalent with respect to the usage amount (1 mol) of the compound (5).

The copper(I) compound is also used as a catalyst, and is not particularly limited. Examples thereof may include copper halides, such as copper chloride, copper bromide, and copper iodide. Of those copper(I) catalysts, copper iodide or copper bromide is preferred, and copper iodide is more preferred from the viewpoint of reactivity.

The usage amount of the copper(I) compound is not particularly limited. The usage amount may be, for example, typically from about 0.001 molar equivalent to about 0.5 molar equivalent, preferably from about 0.005 molar equivalent to about 0.05 molar equivalent with respect to the usage amount (1 mol) of the compound (5).

The base is not particularly limited. Examples thereof may include sodium carbonate, potassium carbonate, cesium carbonate, sodium hydroxide, triethylamine, diethylamine, tetramethylethylenediamine (TMEDA), and sodium hydride. Of those bases, triethylamine, diethylamine, or the like is preferred, and triethylamine is more preferred from the viewpoint of reactivity.

The usage amount of the base is not particularly limited. The usage amount may be, for example, typically from about 1 molar equivalent to about 10 molar equivalents, preferably from about 2 molar equivalents to about 4 molar equivalents with respect to the usage amount (1 mol) of the compound (5).

The usage amount of the compound (6) and the usage amount of the compound (7) are also not particularly limited. The compound (6) or the compound (7) may be used at, for example, the following ratio with respect to 1 mol of the usage amount of the compound (5): the usage amount of any such compound is typically from about 0.8 molar equivalent to about 5 molar equivalents, preferably from about 1 molar equivalent to about 1.5 molar equivalents.

The efficiency of the reaction for the production of the compound (2) can be improved by using any other catalyst, such as 2-(di-tert-butylphosphino)-1-phenylindole (PIntB), separately from the copper(I) compound and the palladium catalyst, and performing the reaction in tetramethylethylenediamine (TMEDA) with the other catalyst as a base.

The usage amount of such other catalyst is not particularly limited. The usage amount may be, for example, typically from about 0.01 molar equivalent to about 0.5 molar equivalent, preferably from about 0.1 molar equivalent to about 0.5 molar equivalent with respect to the usage amount (1 mol) of the compound (5).

Conditions for the cross-coupling reaction are not particularly limited. For example, conditions used in this member of reaction may be appropriately adopted. Such conditions may be typically, for example, the following conditions: the compound (5) and the compound (6) or (7) are appropriately cooled or warmed to from about 30° C. to about 80° C. in a solvent, such as a water-acetone mixed solvent, a water-1,4-dioxane mixed solvent, a water-tetrahydrofuran mixed solvent, a water-dimethoxyethane mixed solvent, a water-acetonitrile mixed solvent, N,N-dimethylformamide, N,N-dimethylacetamide, dimethyl sulfoxide, or a water-tetramethylethylenediamine mixed solvent, under an argon atmosphere.

In order to obtain the target product compound (2) with high purity, a commonly used isolating step and/or a commonly used purifying step may be adopted after the completion of the reaction while the steps are appropriately combined. Specific examples of the isolating or purifying step may include chromatography, recrystallization, extraction, and distillation.

The compound (5), the compound (6), and the compound (7) are each a compound easily produced from a known compound in conformity with a known method. For example, the compound (5) may be produced from the following compound (8) serving as a starting raw material by adopting a known cross-coupling reaction while appropriately modifying the reaction.

Specifically, the compound (5) may be produced by a method involving causing the compound (8) represented by the following formula (8)

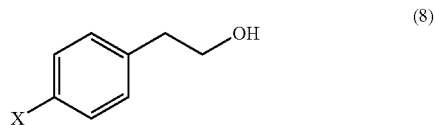

(8)

and a compound (9) represented by the following formula (9) to react with each other in the presence of a base.

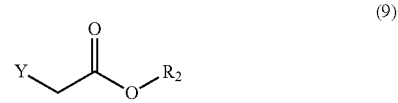

(9)

X in the formula (8) is the same as the X represented in the formula (5).

Y in the formula (9) represents a halogen atom.

The halogen atom represented by the Y is not particularly limited. The atom may be, for example, a chlorine atom, a bromine atom, a fluorine atom, or an iodine atom. The halogen atom (X) and the halogen atom (Y) may be the same atom, or may be different atoms.

The base is not particularly limited. Examples thereof may include sodium carbonate, potassium carbonate, cesium carbonate, sodium hydroxide, triethylamine, tetramethylethylenediamine (TMEDA), and sodium hydride. Of those bases, triethylamine, diethylamine, or the like is preferred, and triethylamine is more preferred from the viewpoint of reactivity.

The usage amount of the base is not particularly limited. The usage amount may be, for example, typically from about 1 molar equivalent to about 5 molar equivalents, preferably from about 1.5 molar equivalents to about 3 molar equivalents with respect to the usage amount (1 mol) of the compound (8).

Conditions for the cross-coupling reaction are not particularly limited. For example, conditions frequently used in this kind of reaction may be appropriately adopted. Such conditions may be typically, for example, the following conditions: the compound (8) and the compound (9) are appropriately cooled or warmed in a solvent, such as tetrahydrofuran, to a temperature equal to or less than the boiling point of the solvent, for example, from about 30° C. to about 66° C.

In order to obtain a target product compound with high purity, a commonly used isolating step and/or a commonly used purifying step may be adopted after the completion of the reaction while the steps are appropriately combined. Specific examples of the isolating or purifying step may include chromatography, recrystallization, extraction, and distillation.

III. Peptide Nucleic Acid

A peptide nucleic acid (3) is a tolan-modified peptide nucleic acid represented by the following formula (3)

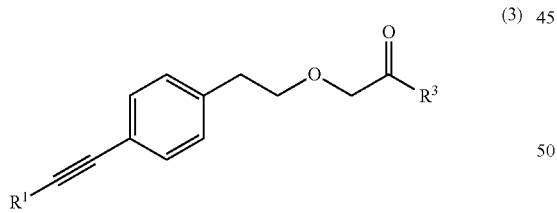

(3)

As described above, $R^1$ in the formula (3) represents a phenyl group that may have 1 to 5 substituents, or a naphthyl group that may have 1 to 7 substituents.

$R^3$ represents a peptide nucleic acid residue.

The peptide nucleic acid residue may be a residue obtained by removing a hydrogen atom from an amide group at the N-terminal of a peptide nucleic acid, and is not particularly limited.

The peptide nucleic acid is a polymer. Monomers forming the polymer are amino acids having bases typified by adenine, cytosine, guanine, thymine, uracil, and the like as respective side chains thereof. Such amino acids may each be a compound having an amino group and a carboxyl group (amino acid in a broad sense). In addition, a polymer obtained by the peptide bonding of such monomers is the peptide nucleic acid.

The polymerization number of such peptide nucleic acid is not particularly limited. For example, the polymerization number may be set to any integer of from 6 to 25. The polymerization number is preferably an integer of from 8 to 23, more preferably an integer of from 10 to 21.

Bases in the monomers may be identical to or different from each other. Accordingly, a base sequence in the peptide nucleic acid is not particularly limited. In particular, a portion where the amino acids are subjected to peptide bonding is sometimes referred to as "main chain".

Such peptide nucleic acid is a compound having such a property as to form a complementary strand with a nucleic acid, such as DNA or RNA, or any other peptide nucleic acid through their bases. The peptide nucleic acid is preferably a compound having such a property as to form a complementary strand while forming a double helix structure.

Such peptide nucleic acid residue may be, for example, a peptide nucleic acid residue represented by the following formula (4).

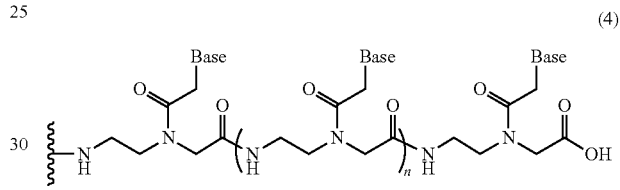

(4)

The Bases in the formula (4) are identical to or different from each other, and each represent adenine, thymine, guanine, cytosine, or uracil.

n in the formula (4) means an integer of from 6 to 25. The n preferably means an integer of from 8 to 23, and more preferably means an integer of from 10 to 21.

When the Bases in the formula (4) each represent adenine, a group represented by the following formula is bonded.

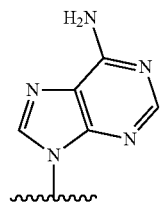 [SMILES: *n1cnc2c(N)ncnc21]

When the Bases in the formula (4) each represent thymine, a group represented by the following formula is bonded.

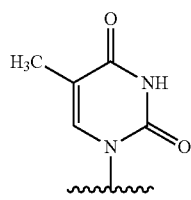

When the Bases in the formula (4) each represent guanine, a group represented by the following formula is bonded.

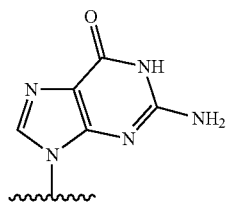 [SMILES: *n1cnc2c(=O)[nH]c(N)nc21]

When the Bases in the formula (4) each represent cytosine, a group represented by the following formula is bonded.

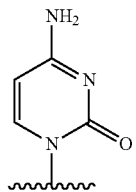 [SMILES: *n1ccc(N)nc1=O]

When the Bases in the formula (4) each represent uracil, a group represented by the following formula is bonded.

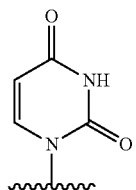 [SMILES: *n1ccc(=O)[nH]c1=O]

The peptide nucleic acid residue may include an amino acid residue and/or a spacer. That is, an arbitrary amino acid residue and/or an arbitrary spacer may be bonded to the peptide nucleic acid residue. Here, the term "bond" means a peptide bond.

A specific amino acid residue to be bonded to the peptide nucleic acid residue is not particularly limited. The residue is, for example, a lysine residue, a histidine residue, or an arginine residue having an amino group on a side chain thereof. Of those, a lysine residue is preferably arranged. The number of the amino acid residues to be bonded to the peptide nucleic acid residue is not particularly limited. The number may be typically set to from about 1 to about 10, and is preferably set to from about 1 to about 5.

The spacer to be bonded to the peptide nucleic acid residue is not particularly limited. Examples thereof may include compounds each having a carboxyl group and an amide group (so-called amino acids in a broad sense).

The spacer may be specifically, for example, a compound (10) represented by the following formula (10).

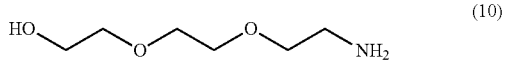

(10)

Further, an oligomer or a polymer using the compound as a monomer may be used as the spacer.

The polymerization number of the oligomer or the polymer given as an example of the spacer is not particularly limited. The polymerization number may be set to, for example, from about 2 to about 100, and is set to preferably from about 2 to about 50, more preferably from about 2 to about 10, still more preferably from about 2 to about 5, most preferably 2.

The position of the amino acid residue or the spacer to be bonded to the peptide nucleic acid residue is not particularly limited. The amino acid residue or the spacer may be typically arranged in the peptide nucleic acid residue or at the C-terminal thereof. The amino acid residue or the spacer is preferably arranged at the C-terminal of the peptide nucleic acid residue out of the positions.

The amino acid residue and/or the spacer to be bonded to the peptide nucleic acid residue may be bonded to the peptide nucleic acid residue such that the amino acid residue and the spacer are polymerized by a peptide bond, or may be separately bonded thereto. In particular, it is preferred that the spacer be bonded to the peptide nucleic acid residue while being polymerized (i.e., in an oligomer form or a polymer form), and it is most preferred that the oligomer or the polymer be bonded to the peptide nucleic acid residue so as to be sandwiched between the peptide nucleic acid residue and the amino acid residue by a peptide bond.

The peptide nucleic acid (3) may include a peptide nucleic acid subjected to a chemical modification. Specific examples of the chemical modification include acetylation, formylation, myristoylation, pyroglutamation, alkylation, glycosylation, amidation, acylation, hydroxylation, deamination, prenylation, palmitoylation, phosphorylation, biotinylation, and succinimidation. The number of kinds of the chemical modifications to be performed on the peptide nucleic acid (3) is not limited to one, and two or more kinds of the chemical modifications may be performed thereon. Of the chemical modifications, the acetylation, the alkylation, the glycosylation, the biotinylation, or the like is preferred, and the biotinylation is most preferred. In addition, when two or more kinds of the chemical modifications are combined, at least the biotinylation is preferably included in the two or more kinds.

The position on which the chemical modification is performed is not particularly limited. For example, the chemical modification is preferably performed on such amino acid residue to be arranged in the peptide nucleic acid residue as described above.

(Production Method)

A method of producing the peptide nucleic acid (3) is not particularly limited. For example, a peptide nucleic acid residue (PNA oligomer) is synthesized by using various bases forming the peptide nucleic acid, the bases being represented by the following formulae, as raw materials according to an Fmoc solid-phase synthesis method. Next, respective Tolan Compounds 1 to 6 to be produced in Production Example 1 to be described below are used as raw materials, and the raw material compounds are each introduced into the N-terminal or C-terminal of the synthesized peptide nucleic acid residue by a solid-phase synthesis method in a dehydration condensation manner through a peptide bond. Thus, the peptide nucleic acid (3) can be produced. A detailed production method is described in Production Example 2 to be described later.

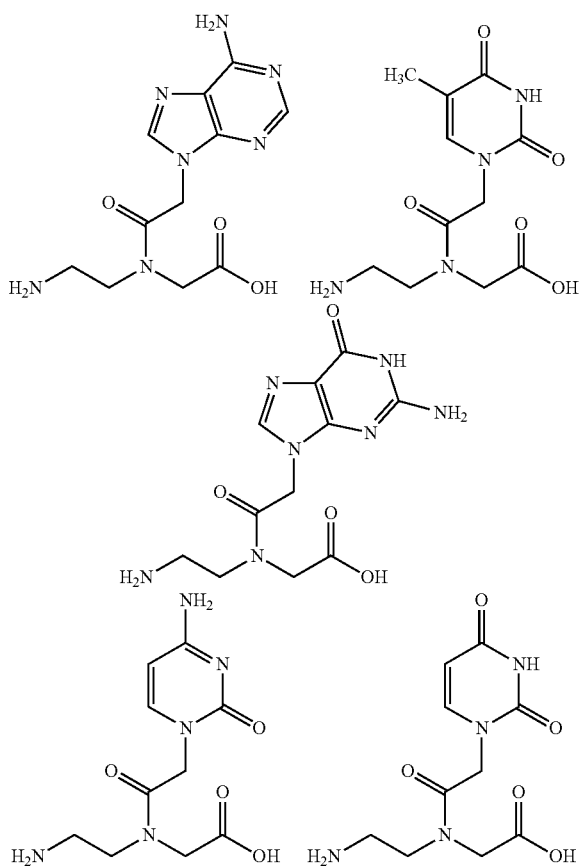

As described in Examples to be described later, the peptide nucleic acid (3) of the present invention suppresses the formation of a double strand non-specific to a single-base-mismatched sequence, and has higher sequence specificity to a target base sequence of interest. Accordingly, the peptide nucleic acid can be utilized as a molecule useful in a gene sequence diagnosis, the molecule being capable of strictly discriminating the matching or mismatching of a pair of bases adjacent to each other.

In other words, according to the peptide nucleic acid (3) of the present invention, the detection of single-base mutation (detection of SNPs) can be more strictly performed, and a measurement method or a diagnostic method having higher accuracy can be provided by utilizing the approach.

VI. Kit

A kit includes the peptide nucleic acid (3). Of the peptide nucleic acids (3), a biotinylated peptide nucleic acid having a lysine residue at its C-terminal, the lysine residue having biotin bonded to its ε-amino group, is preferred.

A constituent except the peptide nucleic acid (3) in the kit is not particularly limited. The constituent may be, for example, a test strip having arranged therein various members needed at the time of the production of a kit based on an immunochromatography (ICA) method. Examples of such members may typically include a sample-dropping portion (also referred to as "sample pad"), a labeled antibody-containing portion (also referred to as "conjugate pad"), a detecting portion (also referred to as "judging portion"), a controlling portion, and an absorbing portion.

Materials typically used in the art, such as nitrocellulose and latex, may be used for the respective members to be arranged in the test strip. In addition, the arrangement of the respective members may be determined on the basis of a technology typically used in the art. In addition, a substance to be incorporated into each of the members may be determined on the basis of a technology typically used in the art.

For example, a substance for capturing a composite containing a substance to be detected and the peptide nucleic acid (3) of the present invention as constituent components is preferably arranged in the detecting portion. Specifically, when the biotinylated peptide nucleic acid is used, an anti-biotin antibody or an avidin compound known to be efficiently bonded to biotin is preferably arranged in the detecting portion for efficiently capturing the composite.

The applications of the kit are not particularly limited. For example, the kit can be suitably used in an application where the presence or absence of a drug-resistant bacterium, a drug-resistant virus, a drug-resistant protozoan, a drug-resistant mycoplasma, and the like is detected.

The drug-resistant bacterium is not particularly limited. Examples thereof may include methicillin-resistant *Staphylococcus aureus* (MRSA), vancomycin-resistant *Staphylococcus aureus* (VRSA), vancomycin-intermediate *Staphylococcus aureus* (VISA), multidrug-resistant *Staphylococcus aureus*, vancomycin-resistant *Enterococcus* (VRE), carbapenem-resistant *Pseudomonas aeruginosa*, multidrug-resistant *Pseudomonas aeruginosa* (MDRP), multidrug-resistant *Tubercle bacillus* (MDR-TB), extensively drug-resistant *Mycobacterium tuberculosis* (XDR-TB), penicillin-resistant *Streptococcus pneumoniae* (PRSP), carbapenem-resistant *Klebsiella pneumoniae*, multidrug-resistant *Klebsiella pneumoniae*, multidrug-resistant *Acinetobacter* (MDRA), carbapenem-resistant *Escherichia coli*, cephalosporin-resistant *Escherichia coli*, an NDM-1-producing multidrug-resistant bacterium, a carbapenem-resistant enterobacterium (CRE), a cephalosporin-resistant enterobacterium, R-lactamase-producing ampicillin-resistant *Hemophilus influenzae* (BLPAR), R-lactamase-nonproducing ampicillin-resistant *Hemophilus influenzae* (BLNAR), and penicillinase-producing *Neisseria gonorrhoeae* (PPNG).

The drug-resistant virus is not particularly limited. Examples thereof may include an amantadine-resistant influenza virus, an oseltamivir-resistant influenza virus, and a drug-resistant human immunodeficiency virus.

The drug-resistant protozoan is not particularly limited. An example thereof may be chloroquine-resistant malaria.

The drug-resistant mycoplasma is not particularly limited. An example thereof may be macrolide-resistant mycoplasma.

The extent of the resistance of each of the drug-resistant bacterium, the drug-resistant virus, the drug-resistant protozoan, and the drug-resistant mycoplasma to a drug is not particularly limited. In addition, in order that multidrug resistance may be detected, the kind of the peptide nucleic acid (3) only needs to be appropriately selected in accordance with various resistant drugs that are desired to be detected.

Of the detection of the presence or absence of the drug-resistant bacterium, the drug-resistant virus, and the drug-resistant mycoplasma given as an example of the applications of the kit of the present invention, the detection of the drug-resistant virus is preferred. Of such detection, the detection of a drug-resistant influenza virus is more preferred, and the detection of an oseltamivir-resistant influenza virus is most preferred.

The detection of the virus or the like may be judged on the basis of the presence or absence of the formation of the complementary strand of DNA or RNA in a sample collected from a living body (e.g., a mucosal tissue, such as a swab, or blood) and the peptide nucleic acid (3) of the present invention. The formation of such complementary strand may be performed under a temperature condition with reference to a Tm value calculated on the basis of a CG content in the sequence of the complementary strand.

Accordingly, when the complementary strand is formed as described above, and is then used as the constituent of the kit except the peptide nucleic acid (3) described above (e.g., the test strip), the detection of the presence or absence of the drug-resistant bacterium, the drug-resistant virus, the drug-resistant protozoan, the drug-resistant mycoplasma, and the like serving as one usage mode of the kit can be performed. However, it is preferred that the sample after the formation of the complementary strand be not rapidly cooled.

In such detection of the presence or absence, when a signal by a labeled antibody can be observed in the detecting portion, it can be judged that the drug-resistant bacterium, the drug-resistant virus, the drug-resistant protozoan, the drug-resistant mycoplasma, and the like are present.

EXAMPLES

Now, Examples for describing the present invention in more detail are described. Needless to say, the present invention is not limited to Examples described below.

Production Examples

Production Example 1: Tolan Compound

In Production Example 1 below, a commercial compound was used as it was without being purified unless otherwise stated. In addition, a commercial dehydrated solvent was used as a reaction solvent unless otherwise stated. Unless otherwise stated, 60N (spherical, neutral) 40-50 μm manufactured by Kanto Chemical Co., Inc. was used as silica gel for column chromatography used in the purification of a compound. Silicagel (60 F254) manufactured by MERCK was used as a TLC plate.

The following apparatus were used for the analysis of a product.

Nuclear Magnetic Resonance Spectrum:
JEOL Ltd. JML-LA-400 ($H^1$: 400 MHz; $C^{13}$: 100 MHz)
JEOL Ltd. JML-LA-600 ($H^1$: 600 MHz; $C^{13}$: 150 MHz)
Mass Spectrum:
JEOL Ltd. JMS-T100LC (ESI-TOF-HRMS)

The chemical shift of $H^1$-NMR was determined by using tetramethylsilane (0.00 ppm), chloroform (7.24 ppm), and dimethyl sulfoxide (2.50 ppm) as internal standards. In addition, a chemical shift in the case of $C^{13}$-NMR was determined by using tetramethylsilane (0.00 ppm), chloroform (77.0 ppm), and dimethyl sulfoxide (39.7 ppm) as internal standards.

Production Example 1-1 Tolan Compound 1:
3-(4-(phenylethynyl)phenyl)propanoic acid Tolan Compound 1 represented by the following formula was produced. A detailed production method is described below.

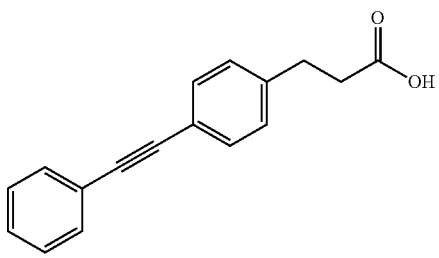

Compound [1] methyl
3-(4-bromophenyl)propanoate

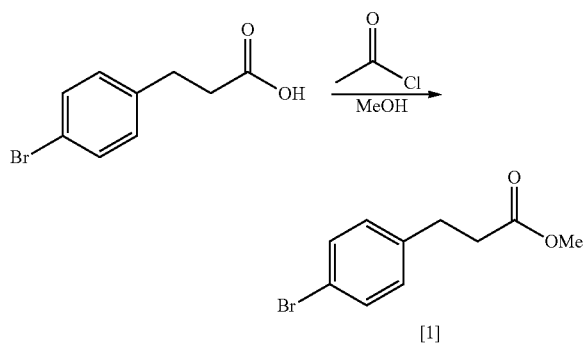

The compound [1] was produced in accordance with the foregoing reaction scheme. Details about the scheme are described below.

40 mL of methanol was loaded into a reaction vessel, and was cooled to 0° C. under an Ar atmosphere. 3.8 mL of acetyl chloride (41.9 mmol) was dropped into the vessel, and the mixture was stirred for 10 minutes at 0° C. Next, 4.0 g of 3-(4-bromophenyl)propanoic acid (52.4 mmol) was added to the mixture, and then the whole was stirred at room temperature for 2 hours. The reaction solution was neutralized with potassium carbonate, and then the solvent was evaporated under reduced pressure. Next, the residue was partitioned between ethyl acetate and water, and the organic layer was washed with brine. After that, magnesium sulfate was added to dry the organic layer, and then the solvent was evaporated under reduced pressure. Thus, 4.35 g of methyl 3-(4-bromophenyl)propanoate serving as a target product was obtained (yield: quant). The resultant compound [1] was used in the next step.

The physical property values of the compound [1] are as follows.

$H^1$-NMR (400 MHz, CDCl$_3$): 7.42-7.39 (m, 2H), 7.09-7.06 (m, 2H), 3.66 (s, 3H), 2.90 (t, 2H), 2.61 (t, 2H)

Compound [2] methyl 3-(4-((trimethylsilyl)ethynyl)phenyl)propanoate

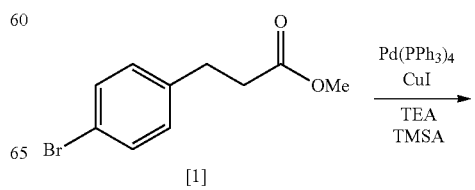

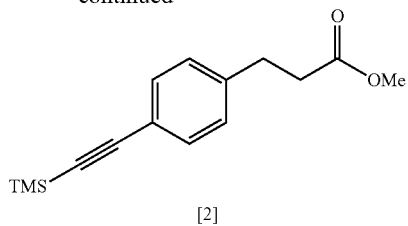

[2]

The compound [2] was produced in accordance with the foregoing reaction scheme. Details about the scheme are described below.

1.0 g of methyl 3-(4-bromophenyl)propanoate described above (4.11 mmol) was loaded into a reaction vessel, and was dissolved in 7 mL of DMF. 156 mg of copper iodide (0.82 mmol), 1.2 mL of triethylamine (8.23 mmol), 475 mg of tetrakis(triphenylphosphine)palladium(0) (Pd(PPh$_3$)$_4$: 0.41 mmol), and 0.74 mL of TMSA (5.35 mmol) were added to the solution in the stated order, and then the mixture was stirred under an Ar atmosphere at 80° C.

After the disappearance of the raw materials had been confirmed by TLC, the reaction solution was filtered with celite. A mixed solvent containing ethyl acetate and hexane at a ratio of 10:1 was added to the filtrate, and the mixture was washed with an aqueous solution of ammonium chloride twice and with brine once. Next, the washed product was dried with magnesium sulfate, and the solvent was evaporated under reduced pressure. Thus, 740 mg of methyl 3-(4-((trimethylsilyl)ethynyl)phenyl)propanoate serving as a target compound was obtained. The resultant compound [2] was used in the next step.

Compound [3] methyl 3-(4-ethynylphenyl)propanoate

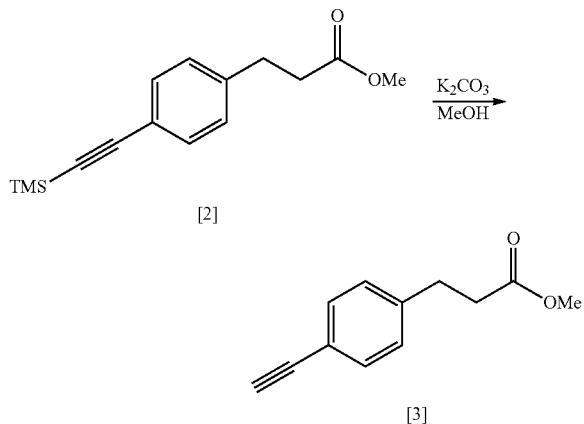

The compound [3] was produced in accordance with the foregoing reaction scheme. Details about the scheme are described below.

740 mg of methyl 3-(4-((trimethylsilyl)ethynyl)phenyl) propanoate described above, 10 mL of methanol, and 780 mg of potassium carbonate were loaded into a reaction vessel, and were stirred at room temperature. After the disappearance of the raw materials had been able to be confirmed by TLC, water was added to the reaction solution, and the mixture was extracted with ethyl acetate three times. The organic layers were combined and washed with brine. The washed product was dried with magnesium sulfate, and the solvent was evaporated under reduced pressure. The residue was purified by column chromatography (hexane: AcOEt=5:1 (v/v)) to provide 243 mg of methyl 3-(4-ethynylphenyl)propanoate serving as a target product (yield: 31%: over 2 steps). The resultant compound [3] was used in the next step.

The physical property values of the compound [3] are as follows.

H$^1$-NMR (400 MHz, CDCl$_3$): 7.40 (d, 2H), 7.14 (d, 2H), 3.64 (s, 3H), 3.06 (s, 1H), 2.90 (t, 2H), 2.61 (t, 2H)

Compound [4] methyl 3-(4-(phenylethynyl)phenyl)propanoate

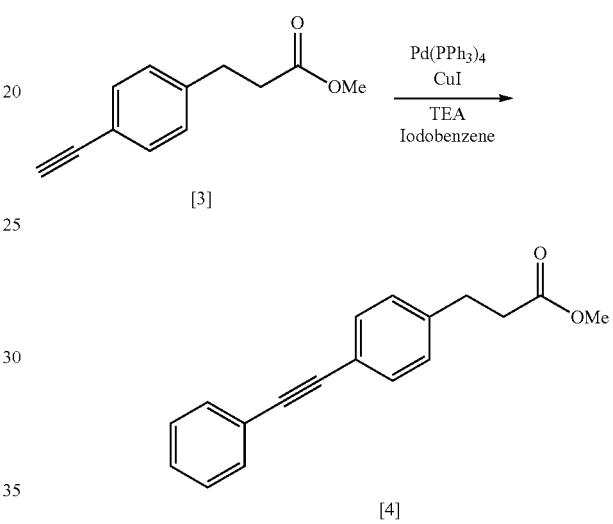

The compound [4] was produced in accordance with the foregoing reaction scheme. Details about the scheme are described below.

243 mg of methyl 3-(4-ethynylphenyl)propanoate described above (1.29 mmol) was loaded into a reaction vessel, and was dissolved in 7 mL of DMF. 156 mg of copper iodide (0.82 mmol), 1.2 mL of TEA (8.23 mmol), 475 mg of tetrakis(triphenylphosphine)palladium(0) (Pd(PPh$_3$)$_4$: 0.41 mmol), and 0.74 mL of TMSA (5.35 mmol) were added to the solution in the stated order, and then the mixture was stirred under an Ar atmosphere at 80° C.

After the disappearance of the raw materials had been confirmed by TLC, the reaction solution was filtered with celite. A mixed solvent containing ethyl acetate and hexane at a ratio of 10:1 was added to the filtrate, and the mixture was washed with an aqueous solution of ammonium chloride twice and with brine once. The washed product was dried with magnesium sulfate, and then the solvent was evaporated under reduced pressure. Thus, 308 mg of methyl 3-(4-(phenylethynyl)phenyl)propanoate serving as a target product was obtained (yield: 90%). The resultant compound [4] was used in the next step.

The physical property values of the compound [4] are as follows.

H$^1$-NMR (400 MHz, CDCl$_3$): 7.51-7.49 (m, 2H), 7.43 (d, 2H), 7.30-7.26 (m, 3H), 7.12 (d, 2H), 3.60 (s, 3H), 2.89 (t, 2H), 2.56 (t, 2H)

Tolan Compound 1;
3-(4-(phenylethynyl)phenyl)propanoic acid

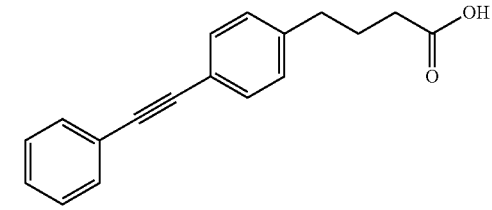

Compound [5] methyl 4-(4-bromophenyl)butanoate

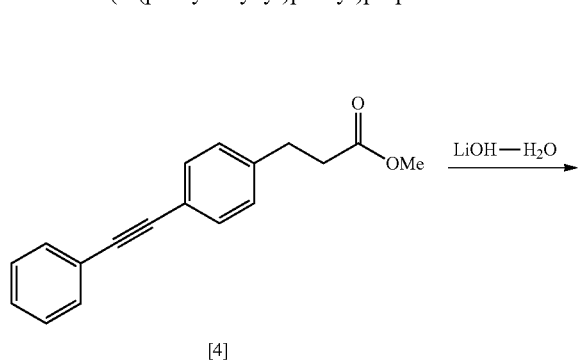

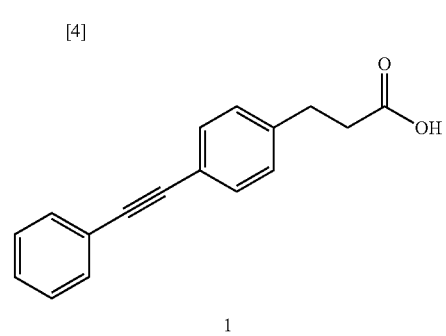

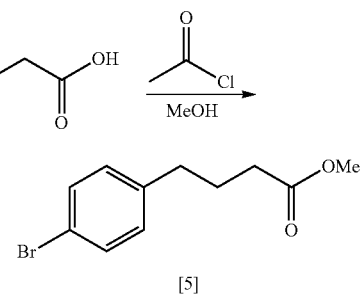

Tolan Compound 1 was produced in accordance with the foregoing reaction scheme. Details about the scheme are described below.

308 mg of methyl 3-(4-(phenylethynyl)phenyl)propanoate described above (1.17 mmol) and 5 mL of THF were loaded into a reaction vessel, and were stirred. 98 mg of lithium hydroxide monohydrate (2.33 mmol) dissolved in 3 mL of purified water was added to the reaction solution, and the mixture was stirred at room temperature.

After the disappearance of the raw materials had been confirmed by TLC, water was added to the reaction liquid, and a 3% aqueous solution of hydrochloric acid was added to adjust the pH of the reaction liquid to less than 1. The reaction liquid was extracted with ethyl acetate three times, and the organic layers were combined and washed with brine. The washed product was dried with magnesium sulfate, and the solvent was evaporated under reduced pressure. Thus, 248 mg of 3-(4-(phenylethynyl)phenyl)propanoic acid (Tolan Compound 1) serving as the final target product was obtained (yield: 85%).

The physical property values of Tolan Compound 1 are as follows.

H[1]-NMR (400 MHz, DMSO-d6): 7.53-7.50 (m, 2H), 7.55 (d, 2H), 7.35-7.30 (m, 3H), 7.18 (d, 2H), 2.95 (t, 2H), 2.68 (t, 2H) ESI HRMS m/z [M+Na]+ calcd 273.0891, found 273.0889

Production Example 1-2 Tolan Compound 2:
4-(4-(phenylethynyl)phenyl)butanoic acid Tolan Compound 2 represented by the following formula was produced. A detailed production method is described below.

The compound [5] was produced in accordance with the foregoing reaction scheme. Details about the scheme are described below.

30 mL of methanol was loaded into a reaction vessel, and was cooled to 0° C. under an Ar atmosphere. 1.8 mL of acetyl chloride (24.7 mmol) was dropped into the vessel, and the mixture was stirred for 10 minutes at 0° C. Next, 2.0 g of 4-(4-bromophenyl)butanoic acid (8.23 mmol) was added to the mixture, and then the whole was stirred at room temperature for 2 hours.

The reaction solution was neutralized with potassium carbonate, and then the solvent was evaporated under reduced pressure. Next, the residue was partitioned between ethyl acetate and water, and the organic layer was washed with brine. After that, magnesium sulfate was added to dry the organic layer, and then the solvent was evaporated under reduced pressure. Thus, 2.12 g of methyl 4-(4-bromophenyl)butanoate serving as a target product was obtained (yield: quant). The resultant compound [5] was used in the next step.

The physical property values of the compound [5] are as follows.

H[1]-NMR (400 MHz, CDCl$_3$): 7.41 (d, 2H), 7.05 (d, 2H), 3.67 (s, 3H), 2.60 (t, 2H), 2.32 (t, 2H), 1.93 (q, 2H)

Compound [6] methyl 4-(4-(phenylethynyl)phenyl)
butanoate

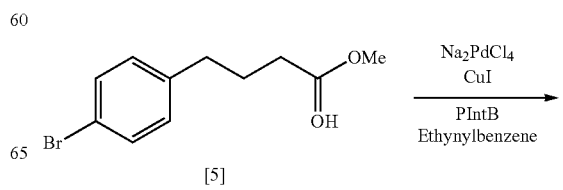

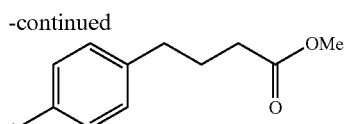

[6]

The compound [6] was produced in accordance with the foregoing reaction scheme. Details about the scheme are described below.

1.0 g of methyl 4-(4-bromophenyl)butanoate described above (3.89 mmol) was loaded into a reaction vessel, and was dissolved in a mixed solvent containing 6 mL of TMEDA and 1 mL of purified water. 10 mg of $Na_2PdCl_4$ (0.04 mmol), 14 mg of copper iodide (0.07 mmol), 28 mg of 2-(di-tert-butylphosphino)-N-phenylindole (PintB; 0.07 mmol), and 0.4 mL of ethynylbenzene (3.53 mmol) were added to the solution in the stated order, and then the mixture was stirred under an Ar atmosphere at 80° C.

After the disappearance of the raw materials had been confirmed by TLC, water was added to the reaction liquid, and the mixture was extracted with ethyl acetate three times. The organic layers were combined, and the resultant was washed with a saturated aqueous solution of ammonium chloride twice and washed with brine. After that, the washed product was dried with magnesium sulfate, and the solvent was evaporated under reduced pressure.

Next, the residue was purified by column chromatography (hexane:AcOEt=4:1 (v/v)) to provide 745 mg of methyl 4-(4-(phenylethynyl)phenyl)butanoate serving as a target product (yield: 71%). The resultant compound [6] was used in the next step.

The physical property values of the compound [6] are as follows.

$H^1$-NMR (400 MHz, $CDCl_3$): 7.51-7.49 (m, 2H), 7.43 (d, 2H), 7.27-7.24 (m, 3H), 7.08 (d, 2H), 3.58 (s, 3H), 2.56 (t, 2H), 2.24 (t, 2H), 1.87 (q, 2H)

Tolan Compound 2;
4-(4-(phenylethynyl)phenyl)butanoic acid

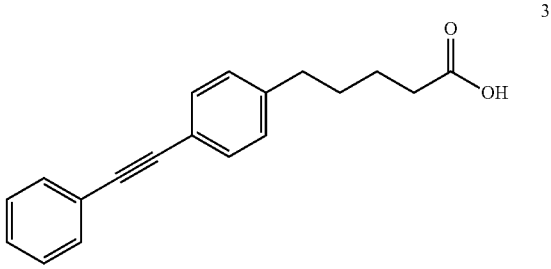 [SMILES: O=C(O)CCCCc1ccc(C#Cc2ccccc2)cc1]

Tolan Compound 2 was produced in accordance with the foregoing reaction scheme. Details about the scheme are described below.

745 mg of methyl 4-(4-(phenylethynyl)phenyl)butanoate described above (2.68 mmol) and 13 mL of THF were loaded into a reaction vessel, and were stirred. 225 mg of lithium hydroxide monohydrate dissolved in 5 mL of purified water was added to the reaction liquid, and the mixture was stirred at room temperature.

After the disappearance of the raw materials had been confirmed by TLC, water was added to the reaction liquid, and a 3% aqueous solution of hydrochloric acid was added to adjust the pH of the reaction liquid to less than 1. The reaction liquid was extracted with ethyl acetate three times, and the organic layers were combined and washed with brine. The washed product was dried with magnesium sulfate, and the solvent was evaporated under reduced pressure. Thus, 700 mg of (4-(4-(phenylethynyl)phenyl) butanoic acid (Tolan Compound 2) serving as the final target product was obtained (yield: 99%).

The physical property values of Tolan Compound 2 are as follows.

$H^1$-NMR (400 MHz, DMSO-d6): 7.56-7.54 (m, 2H), 7.48 (d, 2H), 7.44-7.41 (m, 3H), 7.26 (d, 2H), 2.63 (t, 2H), 2.23 (t, 2H), 1.81 (q, 2H) ESI HRMS m/z $[M+Na]^+$ calcd 287.1043, found 287.1040

Production Example 1-3 Tolan Compound 3:
5-(4-(phenylethynyl)phenyl)pentanoic acid Tolan Compound 3 represented by the following formula was produced.

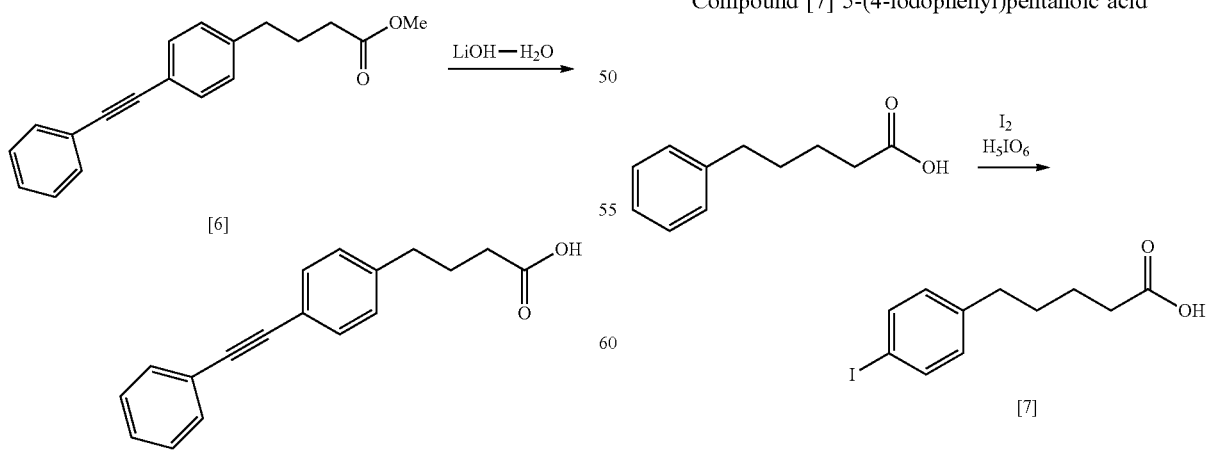

Compound [7] 5-(4-iodophenyl)pentanoic acid

The compound [7] was produced in accordance with the foregoing reaction scheme. Details about the scheme are described below.

1.0 g of 5-phenylpentanoic acid (5.61 mmol), 260 mg of $H_5IO_6$ (1.12 mmol), 280 mg of iodine (2.24 mmol), 0.2 mL of sulfuric acid (10 M), 6 mL of glacial acetic acid, and 1.2 mL of purified water were loaded into a reaction vessel, and were stirred under an Ar atmosphere at 75° C. for 18 hours.

After the reaction solution had been cooled to room temperature, purified water was added to the reaction solution, and the mixture was extracted with chloroform three times. The organic layers were combined, and the resultant was washed with an aqueous solution of sodium thiosulfate twice and with brine once. The washed product was dried with magnesium sulfate, and the solvent was evaporated under reduced pressure.

The residue was dissolved in a trace amount of chloroform, and hexane was added to the solution to perform recrystallization. Thus, 405 mg of 5-(4-iodophenyl)pentanoic acid serving as a target product was obtained (yield: 24%). The resultant compound [7] was used in the next step.

The physical property values of the compound [7] are as follows.

$H^1$-NMR (400 MHz, $CDCl_3$): 7.59 (d, 2H), 6.93 (d, 2H), 2.59 (t, 2H), 2.38 (t, 2H), 1.65 (q, 4H).

Compound [8] methyl 5-(4-iodophenyl)pentanoate

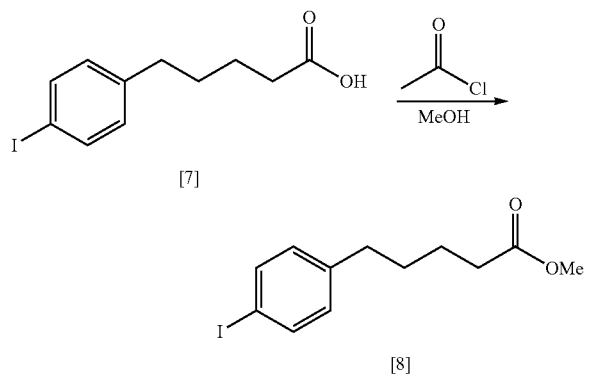

The compound [8] was produced in accordance with the foregoing reaction scheme. Details about the scheme are described below.

5 mL of methanol was loaded into a reaction vessel, and was cooled to 0° C. under an Ar atmosphere. Acetyl chloride (0.3 mL, 4.00 mmol) was dropped into the vessel, and the mixture was stirred for 10 minutes at 0° C. 405 mg of 5-(4-iodophenyl)pentanoic acid (1.33 mmol) described above was added to the mixture, and then the mixture was stirred at room temperature for 2 hours.

Next, the reaction solution was neutralized with potassium carbonate, and then the solvent was evaporated under reduced pressure. The residue was partitioned between ethyl acetate and water, and the organic layer was washed with brine. After that, magnesium sulfate was added to dry the organic layer, and the solvent was evaporated under reduced pressure. Thus, 445 mg of methyl 5-(4-iodophenyl)pentanoate serving as a target product was obtained (yield: quant). The resultant compound [8] was used in the next step.

The physical property values of the compound [8] are as follows.

$H^1$-NMR (400 MHz, $CDCl_3$): 7.55 (d, 2H), 6.89 (d, 2H), 3.63 (s, 3H), 2.54 (t, 2H), 2.30 (t, 2H), 1.62 (m, 4H)

Compound [9] methyl 5-(4-(phenylethynyl)phenyl)pentanoate

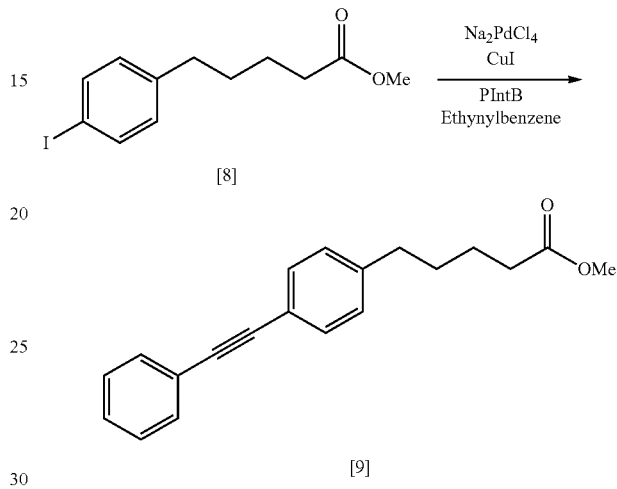

The compound [9] was produced in accordance with the foregoing reaction scheme. Details about the scheme are described below.

445 mg of methyl 5-(4-iodophenyl)pentanoate described above (1.40 mmol) was loaded into a reaction vessel, and was dissolved in a mixed solvent containing 2.5 mL of TMEDA and 0.3 mL of purified water. 3.7 mg of disodium tetrachloropalladate (Na2PdCl4: 0.01 mmol), 5.0 mg of CuI (0.2 mmol), 10 mg of 2-(di-tert-butylphosphino)-N-phenylindole (PIntB; 0.02 mmol), and 0.14 mL of ethynylbenzene (1.30 mmol) were added to the solution in the stated order, and then the mixture was stirred under an Ar atmosphere at 80° C.

After the disappearance of the raw materials had been confirmed by TLC, water was added to the reaction solution, and the mixture was extracted with ethyl acetate three times. The organic layers were combined, and the resultant was washed with a saturated aqueous solution of ammonium chloride twice and washed with brine. After that, the washed product was dried with magnesium sulfate, and the solvent was evaporated under reduced pressure. The residue was purified by column chromatography (hexane:AcOEt=4:1 (v/v)) to provide 395 mg of methyl 5-(4-(phenylethynyl)phenyl)pentanoate serving as a target product (yield: 97%). The resultant compound [9] was used in the next step.

The physical property values of the compound [9] are as follows.

$H^1$-NMR (400 MHz, $CDCl_3$): 7.51-7.49 (m, 2H), 7.43 (d, 2H), 7.31-7.27 (m, 3H), 7.10 (d, 2H), 3.61 (s, 3H), 2.57 (t, 2H), 2.28 (t, 2H), 1.61 (q, 4H)

Tolan Compound 3;
5-(4-(phenylethynyl)phenyl)pentanoic Acid

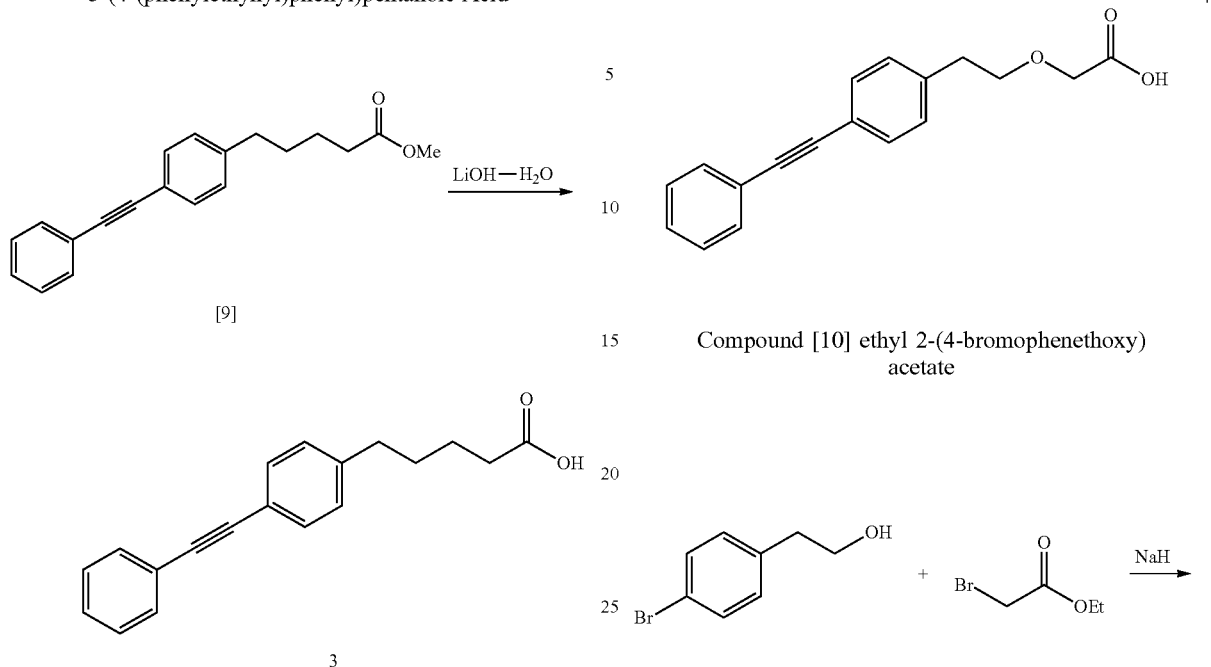

Tolan Compound 3 was produced in accordance with the foregoing reaction scheme. Details about the scheme are described below.

395 mg of methyl 5-(4-(phenylethynyl)phenyl)pentanoate described above (1.35 mmol) and 7 mL of THF were loaded into a reaction vessel, and were stirred. 113 mg of lithium hydroxide monohydrate (2.70 mmol) dissolved in 3 mL of purified water was added to the reaction solution, and the mixture was stirred at room temperature.

After the disappearance of the raw materials had been confirmed by TLC, water was added to the reaction liquid, and a 3% aqueous solution of hydrochloric acid was added to adjust the pH of the reaction liquid to less than 1. The reaction liquid was extracted with ethyl acetate three times, and the organic layers were combined and washed with brine. The washed product was dried with magnesium sulfate, and then the solvent was evaporated under reduced pressure. Thus, 306 mg of (5-(4-(phenylethynyl)phenyl) pentanoic acid (Tolan Compound 3) serving as the final target product was obtained (yield: 81%).

The physical property values of Tolan Compound 3 are as follows.

H[1]-NMR (400 MHz, CDCl$_3$): 7.53-7.51 (m, 2H), 7.45 (d, 2H), 7.35-7.32 (m, 3H), 7.15 (d, 2H), 2.64 (t, 2H), 2.38 (t, 2H), 1.69 (q, 4H) ESI HRMS m/z [M+Na]$^+$ calcd 301.1199, found 301.1198

Production Example 1-4 Tolan Compound 4:
2-(4-(phenylethynyl)phenethoxy)acetic acid Tolan Compound 4 represented by the following formula was produced.

Compound [10] ethyl 2-(4-bromophenethoxy) acetate

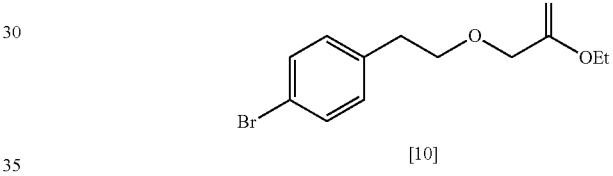

The compound [10] was produced in accordance with the foregoing reaction scheme. Details about the scheme are described below.

220 mg of NaH (in 60% mineral oil; 5.47 mmol) was loaded into a reaction vessel, and was suspended in 15 mL of THF under ice cooling. 1.0 g of 2-(4-bromophenyl)ethan-1-ol (4.97 mmol) was gradually added to the suspension, and the mixture was stirred for 30 minutes.

0.5 mL of ethyl 2-bromoacetate (4.48 mmol) was dropped into the mixture, and the temperature of the reaction liquid was returned to room temperature, followed by stirring for 2 hours. Further, 20 mL of water was added to the reaction liquid, and the mixture was partitioned with ethyl acetate. After that, the aqueous layer was extracted with ethyl acetate three times. The organic layers were combined and washed with brine. The washed product was dried with magnesium sulfate, and the solvent was evaporated under reduced pressure. The residue was purified by column chromatography (hexane:EtOAc=10:1 (v/v)) to provide 785 mg of ethyl 2-(4-bromophenethoxy)acetate serving as a target product (yield: 55%). The resultant compound [10] was used in the next step.

The physical property values of the compound [10] are as follows.

H[1]-NMR (400 MHz, CDCl$_3$): 7.35 (d, 2H), 7.09 (d, 2H), 4.15 (t, 2H), 4.02 (s, 2H), 3.69 (t, 2H), 2.84 (t, 2H), 1.22 (t, 3H)

Compound [11] ethyl 2-(4-(phenylethynyl)phenethoxy)acetate

Tolan Compound 4; 2-(4-(phenylethynyl)phenethoxy)acetic acid

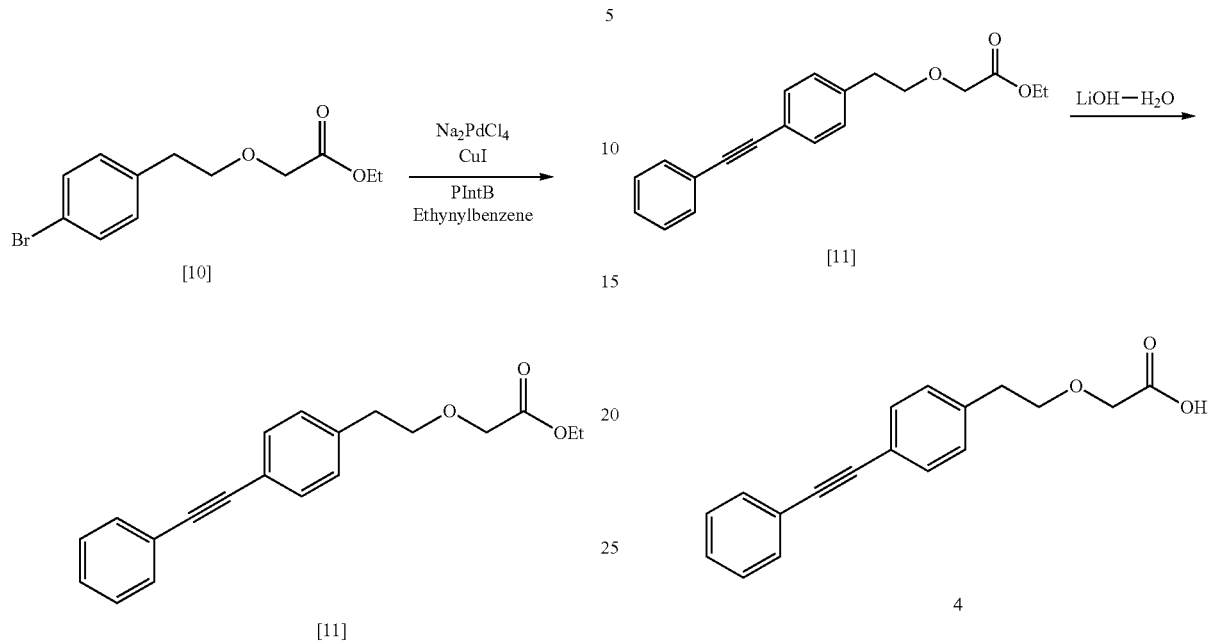

The compound [11] was produced in accordance with the foregoing reaction scheme. Details about the scheme are described below.

785 mg of ethyl 2-(4-bromophenethoxy)acetate described above (2.73 mmol) was loaded into a reaction vessel, and was dissolved in a mixed solvent containing 5 mL of TMEDA and 0.5 mL of purified water. 7.3 mg of disodium tetrachloropalladate ($Na_2PdCl_4$: 0.02 mmol), 9.5 mg of CuI (0.05 mmol), 20 mg of 2-(di-tert-butylphosphino)-N-phenylindole (PIntB: 0.05 mmol), and 0.27 mL of ethynylbenzene (2.49 mmol) were added to the solution in the stated order, and then the mixture was stirred under an Ar atmosphere at 80° C.

After the disappearance of the raw materials had been confirmed by TLC, water was added to the reaction liquid, and the mixture was extracted with ethyl acetate three times. Next, the organic layers were combined, and the resultant was washed with a saturated aqueous solution of ammonium chloride twice and washed with brine. After that, the washed product was dried with magnesium sulfate, and the solvent was evaporated under reduced pressure.

The residue was purified by column chromatography (hexane:AcOEt=4:1 (v/v)) to provide 676 mg of ethyl 2-(4-(phenylethynyl)phenethoxy)acetate) serving as a target product (yield: 80%). The resultant compound [11] was used in the next step.

The physical property values of the compound [11] are as follows.

$H^1$-NMR (400 MHz, $CDCl_3$): 7.52-7.45 (m, 4H), 7.30-7.18 (m, 5H), 4.15 (q, 2H), 4.02 (s, 2H), 3.69 (t, 2H), 2.84 (t, 2H), 1.22 (t, 3H)

Tolan Compound 4 was produced in accordance with the foregoing reaction scheme. Details about the scheme are described below.

676 mg of ethyl 2-(4-(phenylethynyl)phenethoxy)acetate described above (2.19 mmol) and 8 mL of THF were loaded into a reaction vessel, and were stirred. 185 mg of lithium hydroxide monohydrate (4.38 mmol) dissolved in 4 mL of purified water was added to the reaction solution, and the mixture was stirred at room temperature.

After the disappearance of the raw materials had been confirmed by TLC, water was added to the reaction vessel, and a 3% aqueous solution of hydrochloric acid was added to the reaction vessel to adjust the pH of the reaction liquid to less than 1. The reaction liquid was extracted with ethyl acetate three times, and the organic layers were combined and washed with brine. The washed product was dried with magnesium sulfate, and the solvent was evaporated under reduced pressure. Thus, 583 mg of (2-(4-(phenylethynyl) phenethoxy)acetic acid (Tolan Compound 4) serving as the final target product was obtained (yield: 95%).

The physical property values of Tolan Compound 4 are as follows.

$H^1$-NMR (400 MHz, $CDCl_3$): 7.53-7.50 (m, 2H), 7.46 (d, 2H), 7.35-7.31 (m, 3H), 7.21 (d, 2H), 4.12 (s, 2H), 3.77 (t, 2H), 2.95 (t, 2H) ESI HRMS m/z $[M+Na]^+$ calcd 289.0835, found 289.0827

Production Example 1-5 Tolan Compound 5: 2-(4-(naphthalen-2-ylethynyl)phenethoxy)acetic acid Tolan Compound 5 represented by the following formula was produced.

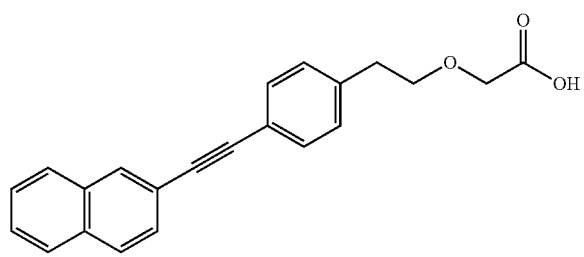

Compound [12] ethyl
2-(4-(naphthalen-2-ylethynyl)phenethoxy)acetate

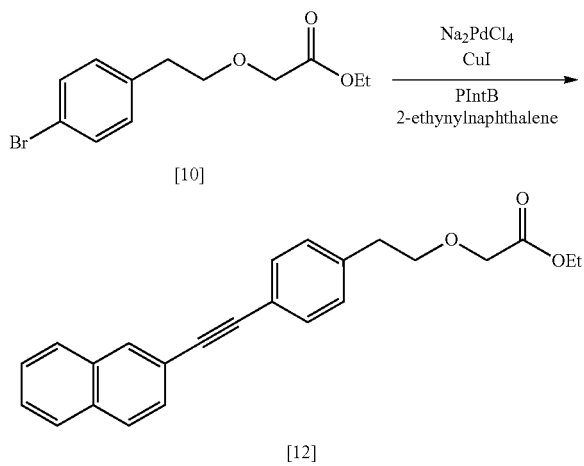

The compound [12] was produced in accordance with the foregoing reaction scheme. Details about the scheme are described below.

110 mg of ethyl 2-(4-bromophenethoxy)acetate described above (0.38 mmol) was loaded into a reaction vessel, and was dissolved in a mixed solvent containing 1 mL of TMEDA and 0.1 mL of purified water. 1.1 mg of disodium tetrachloropalladate ($Na_2PdCl_4$: 3.48 μmol), 1.5 mg of CuI (7.88 μmol), 3.0 mg of 2-(di-tert-butylphosphino)-N-phenylindole (PIntB: 6.97 μmol), and 53 mg of 2-ethynylnaphthalene (0.35 mmol) were added to the solution in the stated order, and then the mixture was stirred under an Ar atmosphere at 80° C.

After the disappearance of the raw materials had been confirmed by TLC, water was added to the reaction liquid, and the mixture was extracted with ethyl acetate three times. Next, the organic layers were combined, and the resultant was washed with a saturated aqueous solution of ammonium chloride twice and washed with brine. After that, the washed product was dried with magnesium sulfate, and the solvent was evaporated under reduced pressure.

The residue was purified by column chromatography (hexane:AcOEt=8:1 (v/v)) to provide 72 mg of (ethyl 2-(4-(naphthalen-2-ylethynyl)phenethoxy)acetate) serving as a target product (yield: 58%). The resultant compound [12] was used in the next step.

The physical property values of the compound [12] are as follows.

$H^1$-NMR (400 MHz, $CDCl_3$): 8.05 (s, 1H), 7.83-7.80 (m, 3H), 7.59-7.49 (m, 5H), 7.24 (d, 2H), 4.23 (q, 2H), 4.12 (s, 2H), 3.83 (t, 2H), 2.99 (t, 2H), 1.22 (t, 3H)

Tolan Compound 5;
2-(4-(naphthalen-2-ylethynyl)phenethoxy)acetic acid

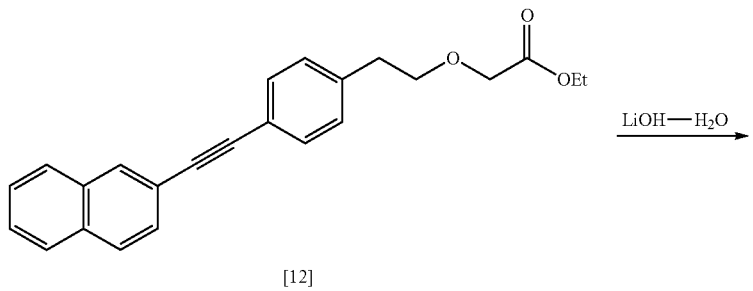

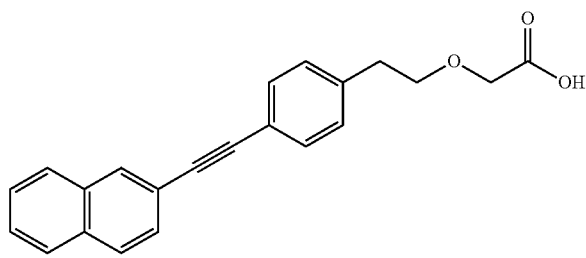

Tolan Compound 5 was produced in accordance with the foregoing reaction scheme. Details about the scheme are described below.

72 mg of ethyl 2-(4-(naphthalen-2-ylethynyl)phenethoxy)acetate (0.20 mmol) and 1.5 mL of THF were loaded into a reaction vessel, and were stirred. Lithium hydroxide monohydrate (0.40 mmol) dissolved in 0.5 mL of purified water was added to the reaction solution, and the mixture was stirred at room temperature.

After the disappearance of the raw materials had been confirmed by TLC, water was added to the reaction vessel, and a 3% aqueous solution of hydrochloric acid was added to the reaction vessel to adjust the pH of the reaction liquid to less than 1. The reaction liquid was extracted with ethyl acetate three times, and the organic layers were combined and washed with brine. The washed product was dried with magnesium sulfate, and then the solvent was evaporated under reduced pressure. Thus, 62 mg of (2-(4-(naphthalen-2-ylethynyl)phenethoxy)acetic acid (Tolan Compound 5) serving as the final target product was obtained (yield: 93%).

The physical property values of Tolan Compound 5 are as follows.

H$^1$-NMR (400 MHz, CDCl$_3$): 8.05 (s, 1H), 7.83-7.80 (m, 3H), 7.59-7.49 (m, 5H), 7.24 (d, 2H), 4.12 (s, 2H), 3.83 (t, 2H), 2.99 (t, 2H) ESI HRMS m/z [M+Na]$^+$ calcd 353.1148, found 353.1143

Production Example 1-6 Tolan Compound 6: 2-(4-((4-cyanophenyl)ethynyl)phenethoxy)acetic acid Tolan Compound 6 represented by the following formula was produced.

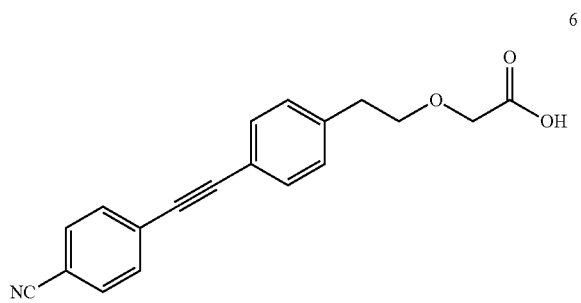 [SMILES: N#Cc1ccc(C#Cc2ccc(CCOCC(=O)O)cc2)cc1]

6

Compound [13] ethyl 2-(4-((4-cyanophenyl)ethynyl)phenethoxy)acetate

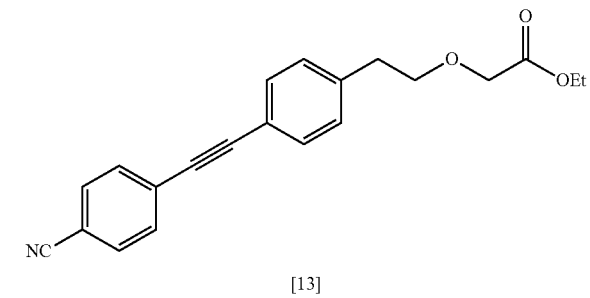

[13]

The compound [13] was produced in accordance with the foregoing reaction scheme. Details about the scheme are described below.

112 mg of ethyl 2-(4-bromophenethoxy)acetate described above (390 μmol) was loaded into a reaction vessel, and was dissolved in a mixed solvent containing 1 mL of TMEDA and 0.1 mL of purified water. 1.1 mg of disodium tetrachloropalladate (Na$_2$PdCl$_4$: 3.48 μmol), 1.5 mg of CuI (7.88 μmol), 3.1 mg of 2-(di-tert-butylphosphino)-N-phenylindole (PIntB: 7.88 μmol), and 140 mg of 4-ethynylbenzonitrile (172 μmol) were added to the solution in the stated order, and then the mixture was stirred under an Ar atmosphere at 80° C.

After the disappearance of the raw materials had been confirmed by TLC, water was added to the reaction liquid, and the mixture was extracted with ethyl acetate three times. The organic layers were combined, and the resultant was washed with a saturated aqueous solution of ammonium chloride twice and washed with brine. After that, the washed product was dried with magnesium sulfate, and the solvent was evaporated under reduced pressure.

The residue was purified by column chromatography (hexane:AcOEt=8:1 (v/v)) to provide 37 mg of ethyl 2-(4-((4-cyanophenyl)ethynyl)phenethoxy)acetate serving as a target product (yield: 29%). The resultant compound [13] was used in the next step.

The physical property values of the compound [13] are as follows.

H$^1$-NMR (400 MHz, CDCl$_3$): 7.64-7.58 (m, 4H), 7.47 (d, 2H), 7.27 (d, 2H), 4.21 (q, 2H), 4.07 (s, 2H), 3.78 (t, 2H), 2.98 (t, 2H), 1.28 (t, 3H).

Tolan Compound 6; 2-(4-((4-cyanophenyl)ethynyl)phenethoxy)acetic acid

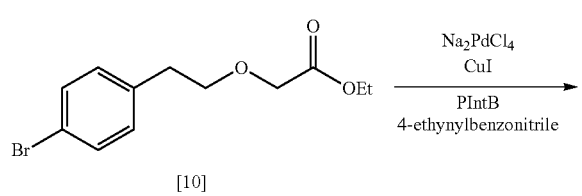

[10]

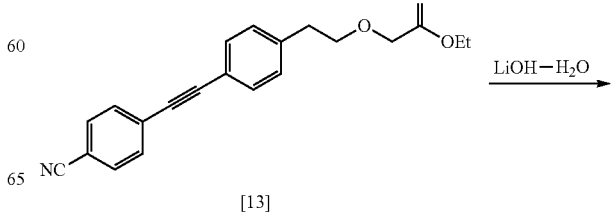

[13]

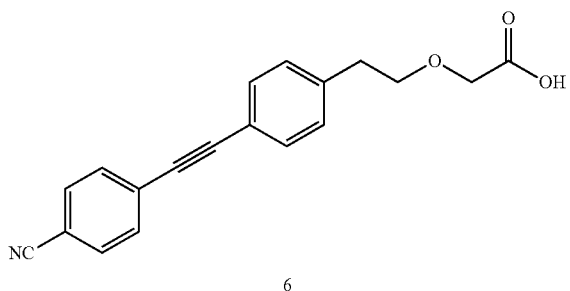

6

Tolan Compound 6 was produced in accordance with the foregoing reaction scheme. Details about the scheme are described below.

35 mg of ethyl 2-(4-((4-cyanophenyl)ethynyl)phenethoxy)acetate (105 μmol) and 1.8 mL of THF were loaded into a reaction vessel, and were stirred. Lithium hydroxide monohydrate (214 μmol) dissolved in 0.5 mL of purified water was added to the reaction solution, and the mixture was stirred at room temperature.

After the disappearance of the raw materials had been confirmed by TLC, water was added to the reaction vessel, and a 3% aqueous solution of hydrochloric acid was added to the reaction vessel to adjust the pH of the reaction liquid to less than 1. The reaction liquid was extracted with ethyl acetate three times, and the organic layers were combined and washed with brine. The washed product was dried with magnesium sulfate, and the solvent was evaporated under reduced pressure. Thus, 18 mg of 2-(4-((4-cyanophenyl)ethynyl)phenethoxy)acetic acid (Tolan Compound 6) serving as the final target product was obtained (yield: 56%).

The physical property values of Tolan Compound 6 are as follows.

$H_1$-NMR (400 MHz, CDCl$_3$): 7.65-7.60 (m, 4H), 7.49 (d, 2H), 7.24 (d, 2H), 4.11 (s, 2H), 3.82 (t, 2H), 2.98 (t, 2H)

Production Example 2: Peptide Nucleic Acid

Peptide nucleic acids whose N-terminals were modified with the tolan compounds (Tolan Compounds 1 to 6) were synthesized. Specifically, peptide nucleic acids 1 to 6 having sequences shown in Table 1 were synthesized by introducing Tolan Compounds 1 to 6 produced in Production Example 1 described above into the N-terminals of PNA oligomers [K . . . (ATCTCCTCCCTT: SEQ ID NO: 1)], which had been synthesized by an Fmoc solid-phase synthesis method, through solid-phase synthesis.

A NovaSyn (trademark) TGR resin (0.24 mmole/g) was used in the Fmoc solid-phase synthesis method, and the synthesized PNA oligomers were each cut out of the resin with an 80% TFA/m-cresol solution. A target product was purified by HPLC (Inertsil ODS-3: 4.6×150 mm, acetonitrile/water containing 0.1% TFA, acetonitrile 10% to 50% for 80 min.), and the mass of the target product was identified by using a MALDI-TOF-MS apparatus (ultrafleXtreme, Bruker Daltonics).

TABLE 1

| | |
|---|---|
| PNA 1 | K...ATCTCCTCCCTT (SEQ ID No.1)-[Tolan Compound 1] |
| PNA 2 | K...ATCTCCTCCCTT (SEQ ID No.1)-[Tolan Compound 2] |
| PNA 3 | K...ATCTCCTCCCTT (SEQ ID No.1)-[Tolan Compound 3] |
| PNA 4 | K...ATCTCCTCCCTT (SEQ ID No.1)-[Tolan Compound 4] |
| PNA 5 | K...ATCTCCTCCCTT (SEQ ID No.1)-[Tolan Compound 5] |
| PNA 6 | K...ATCTCCTCCCTT (SEQ ID No.1)-[Tolan Compound 6] |

The base sequence (SEQ ID NO: 1) of each PNA shown in Table 1 is described so as to start from its C-terminal on the left and to end with its N-terminal on the right. The symbol "K" shown in Table 1 represents a lysine residue, and means that its N-terminal and the C-terminal of a peptide nucleic acid having adenine (A) are subjected to peptide bonding (represented by the symbol " . . . " in the table). In addition, the symbol "-" in the table means that a carboxyl group in each of Tolan Compounds 1 to 6 and thymine (T) at the N-terminal of the peptide nucleic acid are subjected to peptide bonding.

(1) Synthesis Up to Resin-K

One third (0.08 mmol) of the resin (0.24 mmol/g) was elongated.

(1) Coupling Process 400 mg of the resin was weighed in a 6-milliliter disposable syringe. 3 ml of DMF was loaded into the syringe, and the resin was swollen by stirring the mixture for 15 minutes, followed by the removal of DMF. Next, Fmoc-Lys(Biotin)-OH (15.6 mg: 0.03 mmol), Fmoc-Lys(Cbz)-OH (25.4 mg: 0.06 mmol), HBTU (40.5 mg: 0.30 mmol), and HOBT (113.8 mg: 0.30 mmol) were dissolved in 1.2 ml of a coupling solution (NMM/pyridine (1/44; v/v)/DMF (3/2; v/v)). After that, the solution was added to the resin and the mixture was stirred for 40 minutes. After that, the reaction solution was removed, and the resin was washed with DMF five times.

(2) Capping Process 2 ml of a capping solution (acetic anhydride/2,6-lutidine/DMF (5/6/89; v/v/v)) was added to the resin, and the mixture was stirred for 10 minutes. After that, the solution was removed, and the resin was washed with DMF ten times.

(3) Deprotection Process 2 ml of a deprotection solution (piperidine/DMF (4/6; v/v)) was added to the resin, and the mixture was stirred for 5 minutes. After that, the deprotection solution was collected in an Eppendorf tube, and the resin was washed with DMF ten times. The deprotection solution was diluted by a factor of 40, and an elongation reaction was confirmed by measuring its absorbance at 300 nm.

(2) Synthesis up to Resin-K . . . ATCTCCTCCCTT (SEQ ID NO: 1)

(1) Coupling Process

A monomer having each base to be elongated (0.10 mmol), HBTU (40.5 mg: 0.30 mmol), and HOBT (113.8 mg: 0.30 mmol) were dissolved in 1.2 ml of the coupling solution. After that, the solution was added to the resin and the mixture was stirred for 30 minutes. After that, the reaction solution was removed, and the resin was washed with DMF five times.

(2) Capping Process 2 ml of a capping solution was added to the resin, and the mixture was stirred for 10 minutes. After that, the reaction solution was removed, and the resin was washed with DMF ten times.

(3) Deprotection Process 2 ml of the deprotection solution was added to the resin, and the mixture was stirred for 5 minutes. After that, the reaction solution was removed, and the resin was washed with DMF ten times. The confirmation of each elongation reaction was performed in the same manner as that described above.

(3) Synthesis after Resin-K . . . ATCTCCTCCCTT (SEQ ID NO: 1)

First, 400 mg of the resin synthesized so far was dispensed into a 6-milliliter disposable syringe in portions of about 50 mg each.

(1) Coupling Process

A compound with which the N-terminal of the PNA was to be modified (12.5 µmol), HBTU (5.1 mg: 37.5 µmol), and HOBT (14.2 mg: 37.5 µmol) were dissolved in 200 µl of the coupling solution. After that, the solution was added to the resin and the mixture was stirred for 30 minutes. After that, the reaction solution was removed, and the resin was washed with DMF five times.

(2) Capping Process 1 ml of a capping solution was added to the resin, and the mixture was stirred for 10 minutes. After that, the reaction solution was removed, and the resin was washed with DMF ten times.

(4) Cutting Out of Resin

The resin after the completion of an elongation reaction was washed with $CH_2Cl_2$ ten times, and was then washed with MeOH five times, followed by drying in a vacuum. A resin-removing solution (TFA/m-cresol (4/1; v/v)) was added until the resin was immersed therein, and the solution was stirred for 1 hour. 2 ml of $Et_2O$ was loaded into a 15-milliliter Falcon tube, and the resin-removing solution was added from above the tube to precipitate a product. The resin was washed with $Et_2O$ and the product was recovered. After that, cooling was performed at −80° C. for 10 minutes to deposit the product, and centrifugal separation was performed at 4,400 rpm for 4 minutes to precipitate the product, followed by the removal of $Et_2O$. The operation was further performed twice, and the product was dried in a vacuum.

(5) Purification

Purification was performed by HPLC (Inertsil ODS-3; 4.6×150 mm, acetonitrile/water containing 0.1% TFA, acetonitrile 10% to 50% for 80 min) to provide each target product. After the target product had been identified by using a MALDI-TOF-MS apparatus (ultrafleXtreme, Bruker Daltonics), its purity was identified by detecting the absorbance of a nucleobase through HPLC (Inertsil ODS-3; 1.5×150 mm, acetonitrile/water containing 0.1% TFA, acetonitrile 0% to 50% for 30 min, UV 265 nm).

Experiment Example 1 Analysis of Association Behavior of Tolan Derivative-Modified PNA on Each of Complementary DNA and Non-Complementary DNA The peptide nucleic acids 1 to 6 produced in Production Example 2 were each quantitatively evaluated for association behavior (thermodynamical stability of a double strand) on each DNA, that is, each of complementary DNA and non-complementary DNA by melting temperature measurement.

Measurement of Tm Value of Double Strand of Each of Peptide Nucleic Acids 1 to 6 and Each DNA (Each of Complementary DNA and Non-Complementary DNA)

A ratio "DNA:peptide nucleic acid" between DNA having complementary sequence or DNA having non-complementary sequence (see Table 2) and each of the peptide nucleic acids 1 to 6 was adjusted to 1:1. The concentration of the molecules of each of the nucleic acids at this time was set to 4 µmol/L (20 mM phosphate buffer; pH: 7.4). A change in absorbance of the resultant double strand at 260 nm with temperature was measured with an ultraviolet-visible absorption spectrum-measuring apparatus including 8 consecutive cells by changing the temperature in increments of 0.5° C. per minute within the range of from 5° C. to 95° C. to provide a melting curve. The Tm value of the double strand was calculated from the resultant melting curve by using a median line method.

TABLE 2

| | |
|---|---|
| Complementary DNA | ATGTCCTAGAGGAGGGAATAA (SEQ ID No. 2) |
| Non-complementary DNA | ATGTCCTAGAGGAGGGCATAA (SEQ ID No. 3) <br> \|\|\|\|\|\|\|\|\|\|:\| |
| PNA(Control) | K...ATCTCCTCCCTT (SEQ ID No. 1) |
| PNA1~5 | K...ATCTCCTCCCTT-[Tolan Compound 1-6] (SEQ ID NO: 1) |

The base sequence of each DNA shown in Table 2 is described so as to start from its 5'-terminal on the left and to end with its 3'-terminal on the right. In addition, the base sequence of each PNA shown in Table 2 is described so as to start from its C-terminal on the left and to end with its N-terminal on the right.

The symbol "|" of Table 2 means that DNA sequence and PNA sequence are complementary to each other. The symbol ":" in the table means that when the base in DNA sequence is represented by "A", the sequence and each PNA sequence are complementary to each other, and means that when the base in DNA sequence is represented by "C", the sequence and each PNA sequence are non-complementary to each other.

The Tm value was measured at least three times as described above, and the average±standard deviation of the Tm values was determined.

The results of the calculation of the Tm value [° C.] of the double strand of each of the peptide nucleic acids 1 to 6 and each DNA (each of the complementary DNA and the non-complementary DNA), and a difference (ΔTm value [° C.]) between the Tm value of a complementary double strand and the Tm value of a non-complementary double strand are shown in Table 3.

TABLE 3

| | Tm value (° C.) | | |
| --- | --- | --- | --- |
| | Complementary double strand | Non-complementary double strand | Δ Tm value [° C.] |
| PNA (Control) | 56.6 ± 0.9 | 49.4 ± 0.9 | 7.2 |
| PNA 1 | 59.6 ± 0.6 | 49.9 ± 0.7 | 9.7 |
| PNA 2 | 59.5 ± 0.1 | 49.3 ± 0.7 | 10.2 |
| PNA 3 | 61.8 ± 0.9 | 50.0 ± 0.8 | 11.8 |
| PNA 4 | 62.9 ± 0.3 | 50.0 ± 0.6 | 12.9 |
| PNA 5 | 64.9 ± 0.6 | 50.2 ± 0.9 | 14.7 |
| PNA 6 | 63.2 ± 0.7 | 49.9 ± 0.2 | 13.3 |

As can be seen from the results shown in Table 3, the peptide nucleic acid 1 to the peptide nucleic acid 5 are arranged in order of increasing ΔTm value. In more detail, it has been revealed that with regard to the non-complementary sequence, the Tm value of each of the PNA's is around from 49° C. to 50° C., but in the case of a Tm value based on the complementary sequence, various tolan-modified PNA's show values larger than that when the mere PNA is used, and as a result, the peptide nucleic acid 5 improves the stability and sequence selectivity of the complementary double strand to the largest extent.

In addition, as is apparent from comparison between the peptide nucleic acid 4 and the peptide nucleic acid 6, the peptide nucleic acid 6 obtained by arranging a cyano group at the para position of the benzene ring positioned at the terminal of Tolan Compound 4 of the peptide nucleic acid shows the higher ΔTm value. Accordingly, Experiment Example 2 Evaluations of Association Characteristics Based on Mismatched Base Pair and its Position In Experiment Example 2, discriminabilities (association characteristics) on DNA sequences different from each other in mismatched base pair and its position (see Table 4) were evaluated by using the peptide nucleic acid 5 in which the largest improvements in stability and sequence selectivity of the complementary double strand had been observed in Experiment Example 1 as a peptide nucleic acid.

TABLE 4

| PNA 5 | K...ATCTCCTCCCTT-[Tolan Compound 5] (SEQ ID NO: 1) |
| --- | --- |
| | ||||||||||::: |
| DNA Match | ATGTCCTAGAGGAGGGAATAA (SEQ ID No. 2) |
| DNA MM-1 | ATGTCCTAGAGGAGGGABTAA (SEQ ID No. 4) |
| DNA MM-2 | ATGTCCTAGAGGAGGGBATAA (SEQ ID No. 5) |
| DNA MM-3 | ATGTCCTAGAGGAGGHAATAA (SEQ ID No. 6) |

The base sequence of each of DNA's and the PNA in Table 4 is described so as to start from its C-terminal on the left and to end with its N-terminal on the right. B in the table represents cytosine (C), guanine (G), or thymine (T). H in the table represents adenine (A), cytosine (C), or thymine (T).

As shown in Table 4, a DNA sequence having a mismatch (B) at its 3'-terminal forming a double strand was defined as DNA MM-1, a DNA sequence having a mismatch (B) at a second base from the 3'-terminal was defined as DNA MM-2, and a DNA sequence having a mismatch (H) at a third base from the 3'-terminal was defined as DNA MM-3. Tm value measurement was performed by using those sequences in conformity with the method of Experiment Example 1.

Specifically, the association characteristics of the peptide nucleic acid 5 on the various DNA sequences shown in Table 4 were quantitatively evaluated by the Tm value measurement. First, a sample in which the peptide nucleic acid 5 and a DNA were mixed at a concentration ratio of 1:1 was prepared, and a change in absorbance thereof at 260 nm within the range of from 5° C. to 95° C. was measured to provide a melting curve. The Tm value of the sample was calculated from the resultant melting curve by using a median line method. The Tm value was measured at least three times, and the average and standard deviation of the resultant Tm values were determined. In addition, a ΔTm value [° C.] serving as a difference between the Tm value of the complementary double strand and the Tm value of each of non-complementary double strands (the MM-1, the MM-2, and the MM-3) was calculated. The above-mentioned peptide nucleic acid (control) was used as a control (Ctrl). Those results are shown in Table 5.

TABLE 5

| | | MM-1 | | | MM-2 | | | MM3 | | |
|---|---|---|---|---|---|---|---|---|---|---|
| PNA | Match | T:T | T:G | T:C | T:T | T:G | T:C | C:T | C:A | C:C |
| Ctrl | 56.6 | 57.0 | 57.7 | 53.0 | 56.7 | 56.6 | 49.4 | 54.0 | 53.7 | 52.5 |
| | (±0.9) | (±0.4) | (±0.3) | (±0.9) | (±1.9) | (±1.2) | (±0.9) | (±0.8) | (±0.7) | (±1.1) |
| PNA 5 | 64.9 | 59.5 | 60.1 | 53.3 | 58.5 | 59.2 | 50.2 | 55.4 | 55.2 | 52.8 |
| | (±0.6) | (±0.1) | (±0.3) | (±0.2) | (±0.8) | (±0.9) | (±0.9) | (±0.4) | (±0.5) | (±0.5) |

As shown in Table 5, non-specific stabilizing effects on the non-complementary DNA sequences exhibited by using the peptide nucleic acid 5 were from +0.3° C. to +2.6° C. A non-specific stabilizing effect on a non-complementary sequence in the case of modification with any other aromatic compound (e.g., pyrene or azobenzene) was from +4° C. to +6° C., and hence it was revealed that the peptide nucleic acid 5 exhibited a relatively small non-specific stabilizing effect on a mismatched sequence, though the extent of the effect varied depending on a mismatched base pair and the position at which a mismatch was present.

In addition, as is apparent from FIG. 1, the use of the peptide nucleic acid 5 provided the following results: sequence selectivities were largely improved in all sequences including a sequence that could not even be discriminated with the peptide nucleic acid (control) that was not modified with any tolan compound (5° C. to 8° C.). It is assumed from the foregoing that a sequence selectivity-improving effect exhibited by using the peptide nucleic acid 5 of the present invention, in particular, the peptide nucleic acid 5 is exhibited without any dependence on a DNA sequence of interest.

Experiment Example 3 Assembly of Oseltamivir-Resistant Genome-Detecting Kit Using PNA and its Confirmation As described above, the peptide nucleic acid modified with a tolan compound was found to be capable of performing excellent detection of a single nucleotide polymorphism (single-base mismatch), and hence whether or not the peptide nucleic acid was applicable to a detection kit for an oseltamivir-resistant influenza virus was investigated.

(1) Tm Value Measurement Involving Using DNA and PNA

First, the PNA (control PNA-1) having the sequence "C-terminal>GAGTATTATTTT>N-terminal" (SEQ ID NO: 8) serving as the base sequence complementary to the sequence "5'-terminal>CTCATAATAAAA>3'-terminal" (SEQ ID NO: 7) serving as part of the base sequence of DNA characteristic of the oseltamivir-resistant influenza virus (originally, an influenza virus holds RNA as a genetic substance, but an experiment involving using the DNA is performed as a preliminary experiment) was produced. The used PNA and DNA are shown in Table 6.

In addition, the PNA having the same base sequence as the foregoing, the PNA being modified through the peptide bond using Tolan Compound 5, was produced (PNA 5-1). In more detail, the amide group of the peptide nucleic acid residue having T present at the N-terminal of the control PNA-1 and the carboxyl group of the tolan compound are subjected to peptide bonding (the description of the position represented by the symbol "-" of Table 6). The production method for such PNA 5-1 is the same as, for example, those for the PNA's 1 to 5 described above.

The PNA (PNA 6-1) having the base sequence complementary to the above-mentioned DNA sequence, the PNA being modified through the peptide bond in the same manner as that described above by using Tolan Compound 6 instead of Tolan Compound 5, and the PNA (PNA acr) having the base sequence complementary to the above-mentioned DNA sequence, the PNA being modified through the peptide bond in the same manner as that described above by using the acridine compound having the carboxyl group (N-(2-carboxyethyl)-9-acridinaminium; manufactured by Sigma-Aldrich; L135763), were each produced in the same manner as in the PNA 5-1.

The lysine residue formed of KOOK and the spacer are arranged at the C-terminal of the peptide nucleic acid residue having (G) of each of the PNA's. In more detail, the carboxyl group at the C-terminal and the amide group of the main chain of the lysine residue are subjected to peptide bonding (the description of the position represented by the symbol " . . . " in the table).

Further, the group represented by the following formula is subjected to amide bonding to the carboxyl group of the main chain of the lysine residue (a wavy line portion in the formula is subjected to peptide bonding to the lysine residue). Accordingly, the C-terminal of each of the PNA's shown in Table 6 is the lysine residue shown in the group represented by the following formula.

TABLE 6

| Resistance Virus Base Sequence | CTCATAATAAAA (SEQ ID No. 7)<br>\|\|\|\|\|\|\|\|\|\|\|\| |
|---|---|
| PNA Sequence for Resistance Virus | KOOK..GAGTATTATTTT (Ctrl PNA-1) (SEQ ID NO. 8)<br>KOOK..GAGTATTATTTT-[Tolan Compound 5] (PNA 5-1) (SEQ ID NO. 8)<br>KOOK..GAGTATTATTTT-[Tolan Compound 6] (PNA 6-1) (SEQ ID NO. 8)<br>KOOK..GAGTATTATTTT-[Acridine] (PNA acr) (SEQ ID NO. 8) |
| Sensitive Virus Base Sequence | \|\|\|\|\|\|\|\|:\|\|\|<br>CTCATAATCAAA (SEQ ID No. 9) |

The base sequence of each DNA shown in Table 6 is described so as to start from its 5'-terminal on the left and to end with its 3'-terminal on the right. In addition, the base sequence of each PNA is described so as to start from its C-terminal on the left and to end with its N-terminal on the right. The carboxyl group at the C-terminal of each PNA is amidated. The symbol "|" in the table means that the DNA sequence and the PNA sequence are complementary to each other. The symbol ":" in the table means that the DNA sequence and the PNA sequence are non-complementary to each other.

Results obtained with the mass spectrometer (Ulttaflex III manufactured by Bruker Daltonics) for confirming the presence of the various PNA's produced as described above are shown in Table 7 below.

TABLE 7

|  | Calculated | Found |
|---|---|---|
| Ctrl PNA-1 | 4062.35 | 4063.275 |
| PNA 5-1 | 4374.45 | 40374.435 |
| PNA 6-1 | 4349.68 | 4351.774 |
| PNA acr | 4311.668 | 4311.792 |

In order to investigate association characteristics between the various PNA's shown in Table 6, and the DNA having the base sequence characteristic of an oseltamivir-resistant influenza virus (SEQ ID NO: 7) and the DNA having a base sequence characteristic of an oseltamivir-sensitive influenza virus (SEQ ID NO: 9), Tm values were calculated by the same method as that described in Experiment Example 1. In addition, a difference between a Tm value obtained at the time of the use of SEQ ID NO: 7 and a Tm value obtained at the time of the use of SEQ ID NO: 9 was calculated as a ΔTm value for evaluating the extent of a discrimination of a single-base mismatch. The results are shown in Table 8.

TABLE 8

|  | Tm value [° C.] w/ Resistance DNA | Tm value [° C.] w/ Sensitive DNA | Δ Tm value [° C.] |
|---|---|---|---|
| Ctrl PNA-1 | 53.5 | 48.0 | 5.5 |
| PNA 5-1 | 59.3 | 47.6 | 11.7 |
| PNA 6-1 | 55.7 | 47.1 | 8.6 |
| PNA acr | 55.5 | 47.7 | 7.8 |

As is apparent from the results shown in Table 8, the use of the PNA 5-1 was able to discriminate a single-base mismatch most efficiently because its ΔTm value was as high as 11.7.

(2) Tm Value Measurement Involving Using RNA and PNA

As described above, the influenza virus has an RNA as a genetic substance, and hence Tm values and ΔTm values were calculated in the same manner as in the (1) by using RNA having the sequence formed of 5'-terminal>CUCAUAAUAAAA>3'-terminal (SEQ ID NO: 10) instead of the DNA having the base sequence characteristic of an oseltamivir-resistant influenza virus (SEQ ID NO: 7), and by using an RNA having the sequence formed of 5'-terminal>CUCAUAAUCAAA>3'-terminal (SEQ ID NO: 11) instead of the DNA having the base sequence characteristic of an oseltamivir-sensitive influenza virus (SEQ ID NO: 9). The results are shown in Table 9.

TABLE 9

|  | Tm value [° C.] w/ Resistance RNA | Tm value [° C.] w/ Sensitive RNA | Δ Tm value [° C.] |
|---|---|---|---|
| Ctrl PNA-1 | 51.7 | 40.2 | 11.5 |
| PNA 5-1 | 55.3 | 31.5 | 23.8 |

It can be said from the results shown in Table 9 that even when RNA's are used instead of DNA's, superiority at the time of the use of the PNA 5-1 is satisfactory as ever, and rather its extent is more significant when RNA's are used. Accordingly, a kit using such PNA was produced, and whether or not an influenza-resistant bacterium could be detected with the kit was tested.

(3) Oseltamivir-Resistant Influenza-Judging Kit

Figure 2:
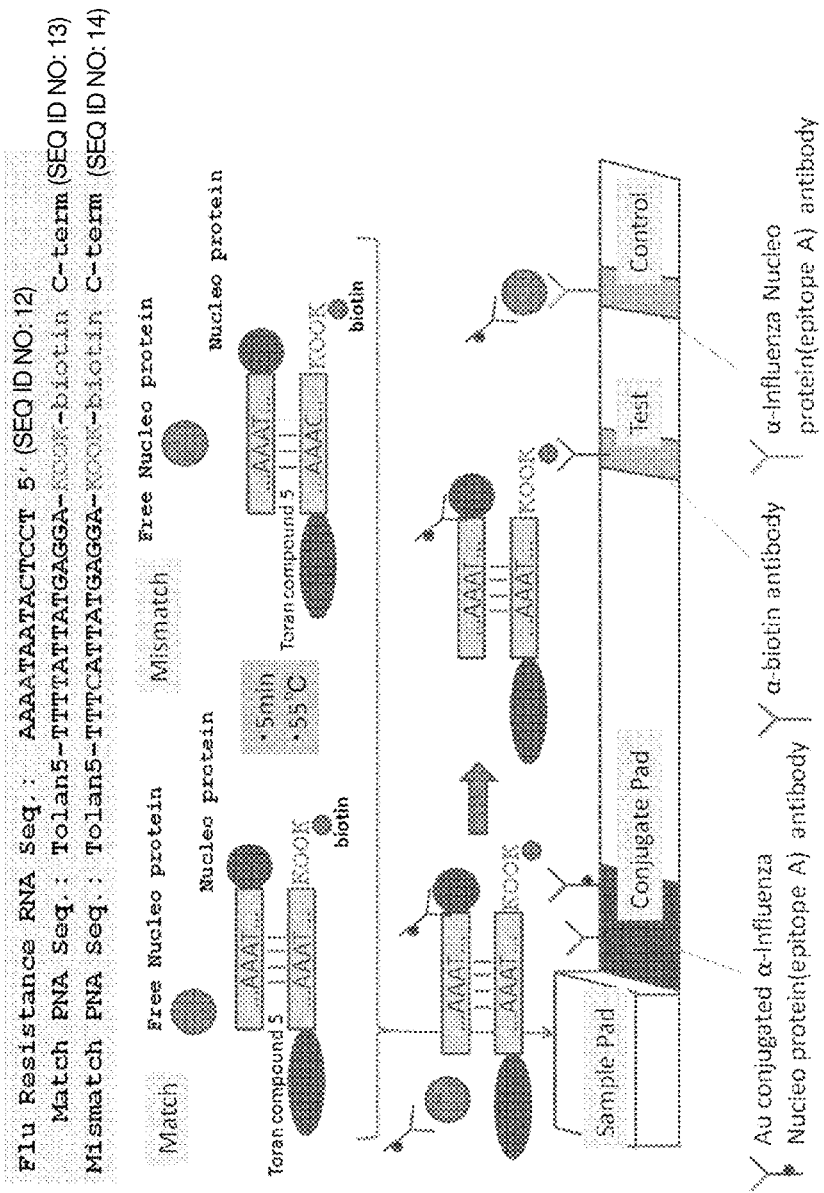
FIG. 2 is a schematic view of an experiment for detecting an oseltamivir-resistant influenza virus according to an immunochromatography method described in Experiment Example 3.

A schematic view of a kit used in the following experiment and the experiment involving using the kit is illustrated in FIG. 2.

Production of Diluted Liquid for Capture Antibody

A goat-derived anti-biotin antibody (manufactured by Bethyl Laboratories, Inc.: A150-111A) and a mouse-derived anti-influenza A monoclonal antibody (manufactured by Abcam PLC: ab66191) were each diluted with sterile water containing 5% sucrose to a final concentration of 0.5 mg/ml.

Production of Judging Portion on Chromatograph Medium

200 μl of the antibody produced in the (1) was applied onto a nitrocellulose membrane measuring 30 cm by 2.5 cm (manufactured by Merck Millipore: HF180MC100) with an applicator (manufactured by Nippn Engineering Co., Ltd.) in a width of 1 mm, and was dried at 55° C. for 5 minutes. After that, the resultant was infiltrated with a 5 mM phosphate buffer (pH: 7.4) containing 0.5% casein for 5 minutes. Next, the infiltrated product was infiltrated with a 5 mM phosphate buffer (pH: 7.4) containing 0.01% SDS for 15 minutes. After that, the infiltrated product was applied to a judging portion on a chromatograph medium, and the resultant was dried at room temperature overnight.

Production of Gold Colloid-Labeled Antibody Solution 0.7 ml of a borate buffer (2 mM; pH: 9.2) was added to 0.1 ml of a gold colloid suspension (manufactured by Winered Chemical Corporation: WRGH-2, average particle diameter: 40 nm) to dilute the suspension. A mouse-derived anti-influenza A monoclonal antibody (manufactured by Abcam PLC: ab110661) was diluted with a 2 mM borate buffer (pH: 9.0) to 0.1 mg/ml. 150 μl of the antibody solution was added to 1 ml of the gold colloid suspension, and the mixture was left at rest at 37° C. for 10 minutes. Next, 0.15 ml of a 2 mM borate buffer (pH: 9.0) containing 10% BSA was added to the mixture, and the whole was left at rest at room temperature for 10 minutes. After that, an ultrasonic wave was applied to the resultant for 30 seconds, and the resultant was subjected to centrifugal separation at 8,000×g for 20 minutes. After the supernatant had been removed, 1 ml of a 2 mM phosphate buffer (pH: 7.4) containing 1.0% BSA and 5% trehalose was added to the residue.

Production of Measuring Kit Based on Immunochromatography Method

40 μl of the gold colloid-labeled antibody solution produced in the foregoing was added to a glass fiber pad measuring 5 mm by 15 mm (manufactured by Merck Millipore). After that, the resultant was dried in a vacuum dryer overnight to produce a conjugate pad. Next, the chromatograph medium produced in the foregoing, a sample pad to which a sample was to be added (manufactured by Merck Millipore: CFSP203000), and an absorbing pad configured to absorb a sample (manufactured by Merck Millipore) were attached to a substrate formed of a packing sheet, and the resultant was cut so as to have a width of 5 mm. Further, the conjugate pad produced in the foregoing was attached to the cut product. Thus, an immunochromatography measuring kit was produced.

Preparation of Developing Liquid

A solution (pH: 7.4) containing a surfactant (NP-40), BSA, FBS, and a phosphate-based buffer was used as a developing liquid for a sample.

Sample Preparation and Measurement

The PNA 5-1 having a sequence complementary to the RNA of the oseltamivir-sensitive influenza virus was diluted with ultrapure water to a concentration of 0.1 μg/μl. 5 μl of the PNA solution thus prepared, and each of 10 μl of a 1.0×106 pfu/ml oseltamivir-resistant influenza virus solution (flu/A/Yokohama/77/H1N1) and 10 μl of an oseltamivir-sensitive influenza virus solution (flu/A/Yokohama/10/H1N1) were left at rest at 55° C. for 5 minutes in the presence of 105 μl of the developing liquid.

After that, the total amount, that is, 120 μl of the resultant RNA solution was developed onto the sample pad of the immunochromatography measuring kit produced in the foregoing without being rapidly cooled. 10 Minutes after that, the test line was visually judged. An experiment in which the control PNA-1 was used instead of the PNA 5-1 was similarly performed. The results are shown in FIG. 3.

As can be seen from the results shown in FIG. 3(A), when the PNA 5-1 was used, a band showing that the PNA 5-1 was positive against the oseltamivir-resistant influenza virus was able to be visually observed on the test line. Meanwhile, when the control PNA-1 was used, the following result was obtained: bands appeared on both the test line and the control line. Accordingly, it was revealed that the control PNA-1 could not be used as a judging kit for the oseltamivir-resistant influenza virus.

Sequence Listing Free Text

SEQ ID NO: 1 represents the base sequence of the peptide nucleic acid (PNA oligomer) (control) (Ctrl). The various peptide nucleic acids represented by SEQ ID NOS: 1 to 6 each have the lysine residue at the 5'-terminal of the base sequence (C-terminal of the peptide nucleic acid).

SEQ ID NO: 2 represents the base sequence that forms a complementary strand with the peptide nucleic acid formed of the base sequence represented by SEQ ID NO: 1 described above, and SEQ ID NOS: 3 to 6 each represent a base sequence that mismatches the base sequence of the peptide nucleic acid formed of the base sequence represented by SEQ ID NO: 1 described above.

The base sequence represented by SEQ ID NO: 7 is obtained by substituting the base sequence characteristic of the oseltamivir-resistant influenza virus with the base sequence of the DNA. SEQ ID NO: 8 represents the base sequence of the PNA having homology to the base sequence represented by SEQ ID NO: 7. The base sequence represented by SEQ ID NO: 9 is obtained by substituting the base sequence characteristic of the oseltamivir-sensitive influenza virus with the base sequence of the DNA.

The base sequence represented by SEQ ID NO: 10 is the base sequence of an RNA characteristic of the oseltamivir-resistant influenza virus. The base sequence represented by SEQ ID NO: 11 is the base sequence of an RNA characteristic of the oseltamivir-sensitive influenza virus.

The invention claimed is:

1. A tolan compound, which is represented by the following formula (1):

(1)

wherein $R^1$ represents a phenyl group or a naphthyl group; the phenyl group may have 1 to 5 substituents that are identical to or different from each other; and the naphthyl group may have 1 to 7 substituents that are identical to or different from each other.

2. The tolan compound according to claim 1, wherein the substituent is an electron-withdrawing group.

3. The tolan compound according to claim 1, wherein the electron-withdrawing group is at least one member selected from the group consisting of a cyano group, a nitro group, an acyl group, a halogen group, a tosyl group, a mesyl group, and a phenyl group.

4. A tolan-modified peptide nucleic acid, which is represented by the following formula (3):

(3)

wherein $R^1$ represents a phenyl group or a naphthyl group; the phenyl group has 1 to 5 substituents that are identical to or different from each other; the naphthyl group has 1 to 7 substituents that are identical to or different from each other; and $R^3$ represents a peptide nucleic acid residue.

5. The peptide nucleic acid according to claim 4, wherein the peptide nucleic acid residue is a residue represented by the following formula (4):

6. The peptide nucleic acid according to claim 4, wherein the substituents are each an electron-withdrawing group.

7. The peptide nucleic acid according to claim 6, wherein the electron-withdrawing group is at least one member selected from the group consisting of a cyano group, a nitro group, an acyl group, a halogen group, a tosyl group, a mesyl group, and a phenyl group.

8. The peptide nucleic acid according to claim 4, wherein the peptide nucleic acid residue comprises an amino acid residue thereof.

9. The peptide nucleic acid according to claim 4, wherein the peptide nucleic acid comprises a chemical modification at one or more amino acid residues.

10. The peptide nucleic acid according to claim 9, wherein the chemical modification is at least one member selected from the group consisting of acetylation, formylation, myristoylation, pyroglutamation, alkylation, glycosylation, amidation, acylation, hydroxylation, deamination, prenylation, palmitoylation, phosphorylation, biotinylation, and succinimidylation.

11. A kit comprising the peptide nucleic acid according to claim 4.

12. A method for detecting a target nucleic acid comprising a single nucleotide polymorphism, comprising contacting a test substance with the tolan-modified peptide nucleic acid according to claim 4, wherein the tolan-modified peptide nucleic acid comprises a sequence complementary to the sequence of the target nucleic acid; and detecting whether a double stranded complex comprising the tolan-modified peptide nucleic acid and the target nucleic acid is formed.

13. A method for detecting a target nucleic acid characteristic of a drug-resistant bacterium, a drug-resistant virus, a drug-resistant protozoan, or a drug-resistant mycoplasma, comprising contacting a test substance with the tolan-modified peptide nucleic acid according to claim 4, wherein the tolan-modified peptide nucleic acid comprises a sequence complementary to the sequence of the target nucleic acid, and detecting whether a double stranded complex comprising the tolan-modified peptide nucleic acid and the target nucleic acid is formed.

14. The method according to claim 13, wherein the drug-resistant virus is an influenza virus.

(4)

wherein the bases are identical to or different from each other, and each represent adenine, thymine, guanine, cytosine, or uracil; and
n is an integer of from 6 to 25.

15. The method according to claim 14, wherein the influenza virus is oseltamivir-resistant.

* * * * *